US011633363B2

United States Patent
Yang et al.

(10) Patent No.: US 11,633,363 B2
(45) Date of Patent: Apr. 25, 2023

(54) FUSION PROTEINS HAVING A TOXIN AND CANCER MARKER, NANOPARTICLES, AND USES RELATED THERETO

(71) Applicant: Emory University, Atlanta, GA (US)

(72) Inventors: Lily Yang, Atlanta, GA (US); Xiangxue Guo, Atlanta, GA (US); Hui Mao, Johns Creek, GA (US); Wei Chen, Atlanta, GA (US)

(73) Assignee: Emory University, Atlanta, GA (US)

( * ) Notice: Subject to any disclaimer, the term of this patent is extended or adjusted under 35 U.S.C. 154(b) by 47 days.

(21) Appl. No.: 16/651,699

(22) PCT Filed: Sep. 27, 2018

(86) PCT No.: PCT/US2018/053156
§ 371 (c)(1),
(2) Date: Mar. 27, 2020

(87) PCT Pub. No.: WO2019/067740
PCT Pub. Date: Apr. 4, 2019

(65) Prior Publication Data
US 2020/0253883 A1 Aug. 13, 2020

Related U.S. Application Data

(60) Provisional application No. 62/563,828, filed on Sep. 27, 2017.

(51) Int. Cl.
| | | |
|---|---|---|
| *C07K 16/00* | (2006.01) | |
| *C12N 5/12* | (2006.01) | |
| *A61K 39/395* | (2006.01) | |
| *A61K 9/51* | (2006.01) | |
| *A61K 47/64* | (2017.01) | |
| *C07K 14/65* | (2006.01) | |
| *C07K 16/28* | (2006.01) | |
| *C07K 16/30* | (2006.01) | |
| *C12N 9/72* | (2006.01) | |
| *A61K 38/00* | (2006.01) | |

(52) U.S. Cl.
CPC ............ *A61K 9/51* (2013.01); *A61K 47/6415* (2017.08); *C07K 14/65* (2013.01); *C07K 16/2863* (2013.01); *C07K 16/30* (2013.01); *C12N 9/6462* (2013.01); *A61K 38/00* (2013.01); *C07K 2319/33* (2013.01); *C07K 2319/55* (2013.01); *C12Y 304/21073* (2013.01)

(58) Field of Classification Search
CPC ................ A61K 47/6415; C07K 16/30; C07K 2319/55; A61P 35/00
See application file for complete search history.

(56) References Cited

U.S. PATENT DOCUMENTS

| | | | |
|---|---|---|---|
| 5,942,602 A * | 8/1999 | Wels .................. | C07K 16/2863 |
| | | | 530/388.22 |
| 9,708,374 B2 | 7/2017 | Mechaly | |
| 9,850,475 B2 | 12/2017 | Collier | |
| 2003/0124147 A1 * | 7/2003 | Vallera .................. | C07K 14/34 |
| | | | 424/178.1 |
| 2006/0034925 A1 | 2/2006 | Au | |
| 2008/0193976 A1 * | 8/2008 | Harding ................ | A61K 47/642 |
| | | | 536/23.7 |
| 2011/0130616 A1 | 6/2011 | Seeney | |
| 2012/0302516 A1 | 11/2012 | Nantz | |
| 2013/0195767 A1 | 8/2013 | Weissleder | |
| 2013/0343996 A1 | 12/2013 | Lee | |
| 2014/0329760 A1 | 11/2014 | Mukhopadhyay | |
| 2014/0377216 A1 * | 12/2014 | Pieczykolan .... | C07K 14/43563 |
| | | | 424/85.1 |
| 2015/0231269 A1 | 8/2015 | Kaittanis | |

FOREIGN PATENT DOCUMENTS

| | | | |
|---|---|---|---|
| CN | 103304638 | 12/2014 | |
| WO | 2001025410 | 4/2001 | |
| WO | 2006042146 | 4/2006 | |
| WO | 2012027494 | 3/2012 | |
| WO | 2012031205 | 3/2012 | |
| WO | 2015001078 | 1/2015 | |
| WO | WO 2015/088977 | * 6/2015 | ............. A61K 47/48 |

OTHER PUBLICATIONS

Bombelli et al. The scope of nanoparticle therapies for future metastatic melanoma treatment, Lancet Oncol, 2014, 15: e22-32.
Huang et al. Casein-coated Iron Oxide Nanoparticles for High MRI Contrast Enhancement and Efficient Cell Targeting, ACS Appl Mater Interfaces, 2013, 5(11): 4632-4639.
Kreitman et al. Phase I Trial of Anti-CD22 Recombinant Immunotoxin Moxetumomab Pasudotox (CAT-8015 or HA22) in Patients With Hairy Cell Leukemia, J Clin Oncol, 2012 30:1822-1828.
Lee et al. Theranostic Nanoparticles with Controlled Release of Gemcitabine for Targeted Therapy and MRI of Pancreatic Cancer, ACS Nano. 2013, 7(3): 2078-2089.
Li et al. Amino—Terminal Fragment of Urokinase Inhibits Tumor Cell Invasion In Vitro and In Vivo: Respective Contribution of the Urokinase Plasminogen Activator Receptor-Dependent or -Independent Pathway, Human Gene Therapy, 2005, 16:1157-1167.

(Continued)

*Primary Examiner* — Mark Halvorson
(74) *Attorney, Agent, or Firm* — Emory Patent Group

(57) ABSTRACT

This disclosure relates to nanoparticles coated with fusion proteins comprising a domain that binds a cancer marker and a domain comprising a toxic polypeptide. In certain embodiments, the targeted cancer marker is urokinase plasminogen activator receptor (uPAR) insulin-like growth factor 1 receptor (IGF1R), EGFR, HER2, and/or other member of the ErbB family of receptors. In certain embodiments, the molecule that binds a cancer marker is an amino terminal fragment of uPA or variant capable of binding uPAR and/or IGF1 or variant capable of binding IGF1R. In certain embodiments, the toxic polypeptide is a bacterial exotoxin.

12 Claims, 5 Drawing Sheets

Specification includes a Sequence Listing.

(56) References Cited

OTHER PUBLICATIONS

Rajagopal et al. Recombinant Toxins That Bind to the Urokinase Receptor Are Cytotoxic without Requiring Binding to the a2-Macroglobulin Receptor, The Journal of Biological Chemistry, 2000, vol. 275, No. 11, Issue, pp. 7566-7573.

Su et al. Expression and purification of recombinant ATF-mellitin, a new type fusion protein targeting ovarian cancer jells, in P. pastoris, Oncology Reports 35: 1179-1185, 2016.

Tsai et al. A novel bispecific ligand-directed toxin designed to simultaneously target EGFR on human glioblastoma cells and uPAR on tumor neovasculature, J Neurooncol, 2011, 103:255-266.

Vallera et al. Targeting Urokinase-Type Plasminogen Activator Receptor on Human Glioblastoma Tumors With Diphtheria Toxin Fusion Protein DTAT, Journal of the National Cancer Institute, 2002, vol. 94, No. 8, 597-606.

Yang et al. Theranostic Nanoparticles Carrying Doxorubicin Attenuate Targeting Ligand Specific Antibody Responses Following Systemic Delivery, Theranostics, 2015, vol. 5, Issue 1, 43-61.

Yang et al. Imageguided and targeted therapy of advanced ovarian cancer using theranostic nanoparticles, In: Proceedings of the 10th Biennial Ovarian Cancer Research Symposium; Sep. 8-9, 2014; Seattle, WA. AACR; Clin Cancer Res 2015, 21(16 Suppl):Abstract Poster-THER-1436.

Zhou et al. In vitro and in vivo anti-tumor activities of anti-EGFR single-chain variable fragment fused with recombinant gelonin toxin, J Cancer Res Clin Oncol (2012) 138:1081-1090.

Zhou et al. IGF1 Receptor Targeted Theranostic Nanoparticles for Targeted and Image-Guided Therapy of Pancreatic Cancer, ACS Nano. 2015, 9(8): 7976-7991.

Zielinski et al. Affitoxin—A Novel Recombinant, HER2-Specific, Anti-Cancer Agent for Targeted Therapy of HER2-Positive Tumors, J Immunother. 2009, 32(8): 817-825.

\* cited by examiner

```
atgggcagcagccatcatcatcatcatcacaactgtgactgtctaaatggaggaacatgt
 M  G  S  S  H  H  H  H  H  H  N  C  D  C  L  N  G  G  T  C
gtgtccaacaagtacttctccaacattcactggtgcaactgcccaaagaaattcggaggg
 V  S  N  K  Y  F  S  N  I  H  W  C  N  C  P  K  K  F  G  G
cagcactgtgaaatagataagtcaaaaggaggtggaggatcaggcgcgcccgagggcggc
 Q  H  C  E  I  D  K  S  K  G  G  G  S  G  A  P  E  G  G
agcctggccgcgctgaccgcgcaccaggcttgccacctgccgctggagactttcacccgt
 S  L  A  A  L  T  A  H  Q  A  C  H  L  P  E  T  F  T  R
catcgccagccgcgcggctgggaacaactggagcagtgcggctatccggtgcagcggctg
 H  R  Q  P  R  G  W  E  Q  L  E  Q  C  G  Y  P  V  Q  R  L
gtcgccctctacctggcggcgcggctgtcgtggaaccaggtcgaccaggtgatccgcaac
 V  A  L  Y  L  A  A  R  L  S  W  N  Q  V  D  Q  V  I  R  N
gccctggccagccccggcagcggcggcgacctgggcgaagcgatccgc
 A  L  A  S  P  G  S  G  G  D  L  G  E  A  I  R
gagcagccggagcaagcccgtctggccctgaccctggccgccgccgagagcgagcgcttc
 E  Q  P  E  Q  A  R  L  A  L  T  L  A  A  A  E  S  E  R  F
gtccggcagggcactggcaacgacgaggccggcgcggccaacggcccggcggacagcggc
 V  R  Q  G  T  G  N  D  E  A  G  A  A  N  G  P  A  D  S  G
gacgccctgctggagcgcaactatcccactggcgcggagttcctcggcgacggcggcgac
 D  A  L  L  E  R  N  Y  P  T  G  A  E  F  L  G  D  G  G  D
gtcagcttcagcacccgcggcacgcagaactggacggtggagcggctgctccaggcgcac
 V  S  F  S  T  R  G  T  Q  N  W  T  V  E  R  L  L  Q  A  H
cgccaactggaggagcgcggctatgtgttcgtcggctaccacggcaccttcctcgaagcg
 R  Q  L  E  E  R  G  Y  V  F  V  G  Y  H  G  T  F  L  E  A
gcgcaaagcatcgtcttcggcggggtgcgcgcgcgcagccaggacctcgacgcgatctgg
 A  Q  S  I  V  F  G  G  V  R  A  R  S  Q  D  L  D  A  I  W
cgcggtttctatatcgccggcgatccggcgctggcctacggctacgcccaggaccaggaa
 R  G  F  Y  I  A  G  D  P  A  L  A  Y  G  Y  A  Q  D  Q  E
cccgacgcacgcggccggatccgcaacggtgccctgctgcgggtctatgtgccgcgctcg
 P  D  A  R  G  R  I  R  N  G  A  L  L  R  V  Y  V  P  R  S
agcctgccgggcttctaccgcaccagcctgaccctggccgcgccggaggcggcgggcgag
 S  L  P  G  F  Y  R  T  S  L  T  L  A  A  P  E  A  A  G  E
gtcgaacggctgatcggccatccgctgccgctgcgcctggacgccatcaccggccccgag
 V  E  R  L  I  G  H  P  L  P  L  R  L  D  A  I  T  G  P  E
gaggaaggcgggcgcctggagaccattctcggctggccgctggccgagcgcaccgtggtg
 E  E  G  G  R  L  E  T  I  L  G  W  P  L  A  E  R  T  V  V
attccctcggcgatccccaccgacccgcgcaacgtcggcggcgacctcgacccgtccagc
 I  P  S  A  I  P  T  D  P  R  N  V  G  G  D  L  D  P  S  S
atccccgacaaggaacaggcgatcagcgccctgccggactacgccagccagcccggcaaa
 I  P  D  K  E  Q  A  I  S  A  L  P  D  Y  A  S  Q  P  G  K
ccgccgaaagacgaactgtaaaagggcgagctcaattcgaagcttgcggccgcactcgag
 P  P  K  D  E  L  -  K  G  E  L  N  S  K  L  A  A  A  L  E
caccaccaccaccaccactgagatccggctgctaac   (SEQ ID NO: 2)
 H  H  H  H  H  H  -  D  P  A  A  N     (SEQ ID NO: 3)
```

FIG. 1

MGSSHHHHHHTSEIVMTQSPATLSLSPGERATLSCRASQSVS
SYLAWYQQKPGQAPRLLIYDASNRATGIPARFSGSGSGTDFT
LTISRLEPEDFAVYYCQQYGSSPITFGQGTRLEIKRSSGGGGS
GAPEGGSLAALTAHQACHLPLETFTRHRQPRGWEQLEQCGY
PVQRLVALYLAARLSWNQVDQVIRNALASPGSGGDLGEAIR
EQPEQARLALTLAAAESERFVRQGTGNDEAGAANGPADSGD
ALLERNYPTGAEFLGDGGDVSFSTRGTQNWTVERLLQAHRQ
LEERGYVFVGYHGTFLEAAQSIVFGGVRARSQDLDAIWRGF
YIAGDPALAYGYAQDQEPDARGRIRNGALLRVYVPRSSLPG
FYRTSLTLAAPEAAGEVERLIGHPLPLRLDAITGPEEEGGRLE
TILGWPLAERTVVIPSAIPTDPRNVGGDLDPSSIPDKEQAISA
LPDYASQPGKPPKDEL (SEQ ID NO: 4)

FIG. 2

FUSION PROTEINS HAVING A TOXIN AND CANCER MARKER, NANOPARTICLES, AND USES RELATED THERETO

CROSS-REFERENCE TO RELATED APPLICATIONS

This application is the National Stage of International Application No. PCT/US 2018/053156 filed Sep. 27, 2018, which claims the benefit of U.S. Provisional Application No. 62/563,828 filed Sep. 27, 2017. The entirety of each of these applications is hereby incorporated by reference for all purposes.

STATEMENT REGARDING FEDERALLY FUNDED RESEARCH

This invention was made with government support under R01CA154129A-01, U01CA151810-02, and RO1CA154846-01 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 15176US ST25.txt. The text file is 25 KB, was created on Mar. 26, 2020, and is being submitted electronically via EFS-Web.

BACKGROUND

Resistance to chemotherapy and radiotherapy is the major challenge in cancer treatment that leads to cancer progress and a poor survival of cancer patients. Many patients fail to respond to the initial treatment of the combination therapy of several chemotherapy drugs (primary resistance) whereas some patients initially respond favorably to a specific therapeutic intervention then develop resistance over time (acquired resistance). Most likely, those tumors are not only resistant to the chemotherapeutic agents that were used to treat the patients, but also respond poorly to other chemotherapy drugs. Thus, there is a need to identify improved cancer treatments.

Several reports explored the application of PE38 toxin for targeted cancer therapy. For example, Kreitman et al. report anti-CD22 recombinant immunotoxin moxetumomab pasudotox. Clin Cancer Res. 2011, 17(20):6398-405. Zielinski et al. report a recombinant, HER2-specific, afftoxin as an anticancer agent for targeted therapy of HER2-positive tumors. J Immunother. 2009, 32(8):817-25

Several reports explored the application of nanoparticles for targeted cancer therapy. For example, Bombelli et al. report nanoparticle therapies for future metastatic melanoma treatment. Lancet Oncol. 2014, 15(1):e22-32. See also Zhou et al. IGF1 Receptor Targeted Theranostic Nanoparticles for Targeted and Image-Guided Therapy of Pancreatic Cancer. ACS Nano, 2015, 9(8):7976-91; Yang et al. Theranostic Nanoparticles Carrying Doxorubicin Attenuate Targeting Ligand Specific Antibody Responses Following Systemic Delivery, Theranostics, 2015, 5(1):43-61; Huang et al. Casein-coated Iron Oxide Nanoparticles for High MRI Contrast Enhancement and Efficient Cell Targeting, ACS applied materials & interfaces, 2013, 5(11):4632-4639. Lee et al. Theranostic Nanoparticles with Controlled Release of Gemcitabine for Targeted Therapy and MRI of Pancreatic Cancer, ACS nano, 2013, 7(3):2078-2089. See WO 2012/031205, WO 2013/0343996, CN103304638.

References cited herein are not an admission of prior art.

SUMMARY

This disclosure relates to nanoparticles coated with fusion protein comprising a domain that binds a cancer marker and a domain comprising a toxic polypeptide. In certain embodiments, the targeted cancer marker is urokinase plasminogen activator receptor (uPAR) insulin-like growth factor 1 receptor (IGF1R), EGFR, HER2, and/or other member of the ErbB family of receptors. In certain embodiments, the molecule that binds a cancer marker is an amino terminal fragment of uPA or variant capable of binding uPAR and/or IGF1, variant capable of binding IGF1R, or peptides or antibody fragment capable of binding EGFR. In certain embodiments, the toxic polypeptide is a bacterial exotoxin such as Pseudomonas exotoxin or fragment.

In certain embodiments the disclosure contemplates an ATF-uPA-spacer-PE 38 fusion peptide comprising: NCD-CLNGGTCVSNKYFSNIHWCNCPKKFGGQHCEIDK-SKGGGGSGAPEGGSLAALTAH
QACHLPLETFTRHRQPRGWEQLEQCGYPVQRLVALY-LAARLSWNQVDQVIRNALASPG
SGGDLGEAIREQPEQARLALTLAAAESER-FVRQGTGNDEAGAANGPADSGDALLERNY PTGAE-FLGDGGDVSFSTRGTQNWTVERLLQAHRQLEER-GYFVGYHGTFLEAAQSIVFG
GVRARSQDLDAIWRGFYIAGDPALAYGYAQDQEP-DARGRIRNGALLRVYVPRSSLPGF YRTSLT-LAAPEAAGEVERLIGHPLPLRLDAITGPEEEGGR-LETILGWPLAERTVVIPSAIPT
DPRNVGGDLDPSSIPDKEQAIS-
ALPDYASQPGKPPKDEL (SEQ ID NO: 1) or variants thereof.

In certain embodiments the disclosure contemplates a ScFvEGFR-spacer-PE 38 fusion peptide comprising:

```
                                              (SEQ ID NO: 5)
TQSPATLSLSPGERATLSCRASQSVSSYLAWYQQKPGQAPRLLIYDASNRA

TGIPARFSGSGSGTDFTLTISRLEPEDFAVYYCQQYGSSPITFGQGTRLEI

KRSSGGGGSGAPEGGSLAALTAHQACHLPLETFTRHRQPRGWEQLEQCGYP

VQRLVALYLAARLSWNQVDQVIRNALASPGSGGDLGEAIREQPEQARLALT

LAAAESERFVRQGTGNDEAGAANGPADSGDALLERNYPTGAEFLGDGGDVS

FSTRGTQNWTVERLLQAHRQLEERGYVFVGYHGTFLEAAQSIVFGGVRARS

QDLDAIWRGFYIAGDPALAYGYAQDQEPDARGRIRNGALLRVYVPRSSLPG

FYRTSLTLAAPEAAGEVERLIGHPLPLRLDAITGPEEEGGRLETILGWPLA

ERTVVIPSAIPTDPRNVGGDLDPSSIPDKEQAISALPDYASQPGKPPKDEL
```

In certain embodiments, the disclosure relates the methods of using fusion proteins or nanoparticles disclosed herein for the treatment of cancer. In certain embodiments, the disclosure relates the methods of using nanoparticles disclosed herein for therapeutic and diagnostic applications. In certain embodiments, the fusion protein comprises SEQ ID NO: 1, 3, 4, 5 or variants thereof.

In certain embodiments, the disclosure relates to targeted delivery of nanoparticles into tumors mediated by fusion proteins disclosed herein. In certain embodiments, the disclosure contemplates nanoparticles comprising fusion proteins having an amino terminal fragment of uPA capable of binding uPAR wherein the nanoparticles further comprises IGF1 as a dual uPAR and IGF1R targeted delivery system.

In certain embodiments, the disclosure contemplates targeted delivery of fusion proteins disclosed herein, such as those comprising SEQ ID NO: 1, 3, 4, 5 or variants, into tumors to reduce the growth of cancerous cells.

In certain embodiments, this disclosure relates to a nucleic acid sequence that encodes a fusion protein disclosed herein. In further embodiments, this disclosure relates to a vector comprising a nucleic acid sequence that encodes a fusion protein disclosed herein. In certain embodiments, this disclosure relates to a cell comprising a vector comprising a nucleic acid sequence that encodes a fusion protein disclosed herein. In certain embodiments, this disclosure relates to an expression system comprising a vector comprising a nucleic acid sequence that encodes a fusion protein disclosed herein.

In certain embodiments, this disclosure relates to a fusion peptide variant (SEQ ID NO: 1, 3, 4, or 5) wherein the variant has at least 45, 50, 55, 60, 65, 70, 75, 80, 85, 90, 92, 95, 98 percent sequence identity or similarity. In certain embodiments, the variant has one or more up to 1, 2, 3, 4, 5, 6, 7, 8, 9, or 10 amino acid substitutions, deletions, and/or additions. In certain embodiments, the substitution is a conserved substitution.

In certain embodiments, this disclosure relates to a fusion protein variant of SEQ ID NO: 1 or 3, that is capable of binding uPAR and reducing the growth of cancer cells. In certain embodiments, this disclosure relates to a fusion protein variant of SEQ ID NO: 4 or 5, that is capable of binding EGFR and reducing the growth of cancer cells.

In certain embodiments, this disclosure relates to a nanoparticle comprising a fusion protein disclosed herein wherein the nanoparticle comprises 20 to 30 or 10 to 40 or 10 to 60 or 10 to 100 of the peptide moieties bound to the exterior of the particle. In certain embodiments, this disclosure relates to a nanoparticle comprising a core comprising iron oxide, gold, or silver as well as polymeric nanoparticles. In certain embodiments, the core has an average diameter of 4 to 10, or 3 to 20, or 3 to 50 nm, or 3 to 500 nm. In certain embodiments, the metallic nanoparticles core have an average diameter of 4 to 10, 4 to 20 nm, or 100 to 300 nm. In certain embodiments, the polymeric nanoparticles 100 to 200 nm, or 50 to 200, or 50 to 500 nm.

In certain embodiments, this disclosure relates to a pharmaceutical composition comprising a nanoparticle disclosed herein and a pharmaceutically acceptable excipient. In further embodiments, this disclosure relates to a pharmaceutical composition, in an aqueous phosphate buffer solution. In certain embodiments, this disclosure relates to a pharmaceutical composition in the form of a pill, capsule, tablet, cream, or aerosol.

In certain embodiments, this disclosure relates to a method of treating cancer comprising administering an effective amount of a fusion protein disclosed herein or a nanoparticle comprising a fusion protein herein, e.g., a peptide comprising SEQ ID NO: 1, 3, 4, 5, or variants thereof, to a subject in need thereof. In certain embodiments, the cancer is selected from carcinoma, lymphoma, blastoma, sarcoma, leukemia, non-small cell lung, squamous cell, small-cell lung, peritoneum, hepatocellular, gastrointestinal, pancreatic, glioma, cervical, ovarian, liver, bladder, hepatoma, breast, colon, colorectal, endometrial, uterine, salivary gland, kidney, liver, prostate, vulval, thyroid, hepatic, and other lymphoproliferative disorders, and various types of head and neck. In certain embodiments, the cancer can be a primary or metastatic tumors.

In certain embodiments, the nanoparticles or fusion proteins disclosed herein are administered intravenously or intraperitoneally.

In further embodiments, this disclosure relates to methods of treating cancer further comprising administering a second nanoparticle and/or chemotherapy agent to the subject.

In certain embodiments, this disclosure relates to a method for cancer diagnosis comprising administering an effective amount of a peptide disclosed herein or nanoparticle disclosed herein to a subject in need thereof and detecting the particle about the area of a cancerous cell or tumor.

BRIEF DESCRIPTION OF THE DRAWINGS

FIG. 1 illustrates a fusion protein disclosed herein (SEQ ID NO: 3) and a nucleic acid (SEQ ID NO: 2) encoding the fusion protein uPAR targeted human ATF (39)-PE38 Toxin.

FIG. 2 illustrates a fusion protein ScFvEGFR-PE38 toxin (SEQ ID NO: 4).

DETAILED DESCRIPTION

Figure 3:
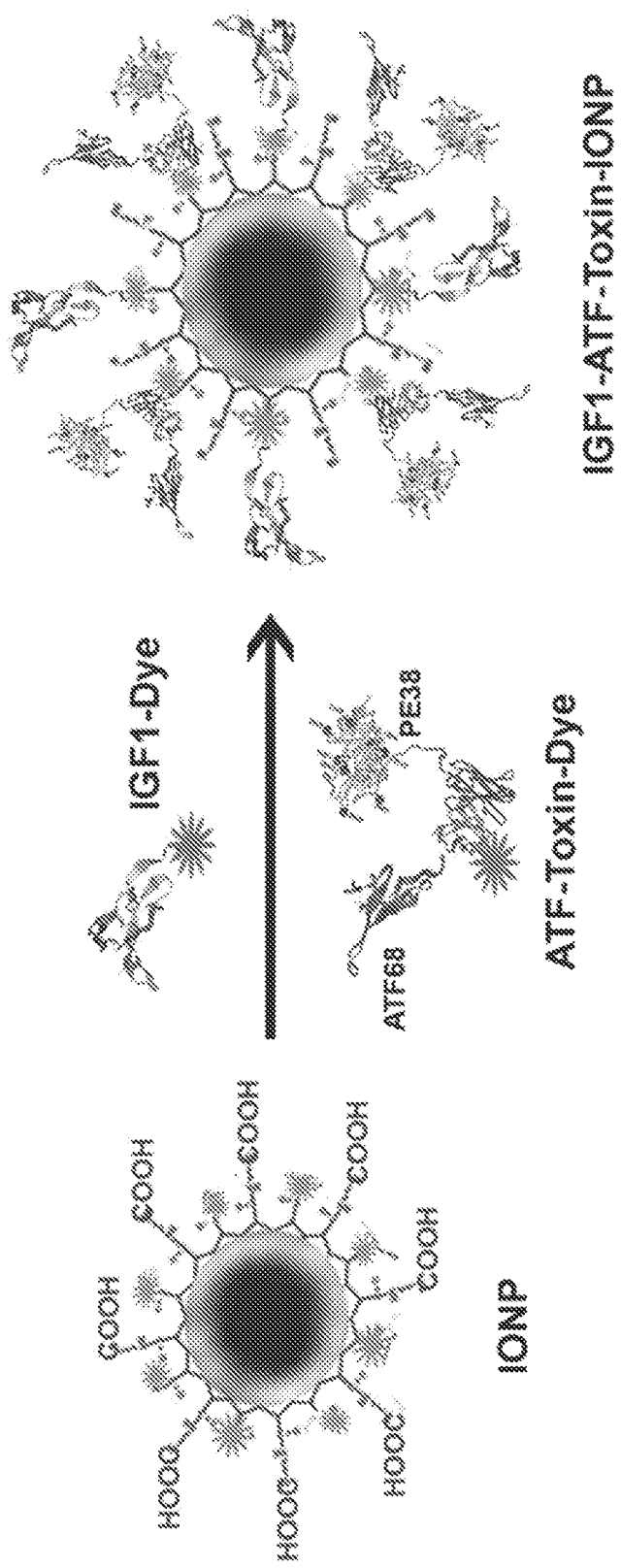
FIG. 3 illustrates conjugation of dual IGF1-IR and uPAR targeted, NIR-830 dye-IGF1 and ATF-Toxin to an amphiphilic polymer coated IONPs.
Figure 4:
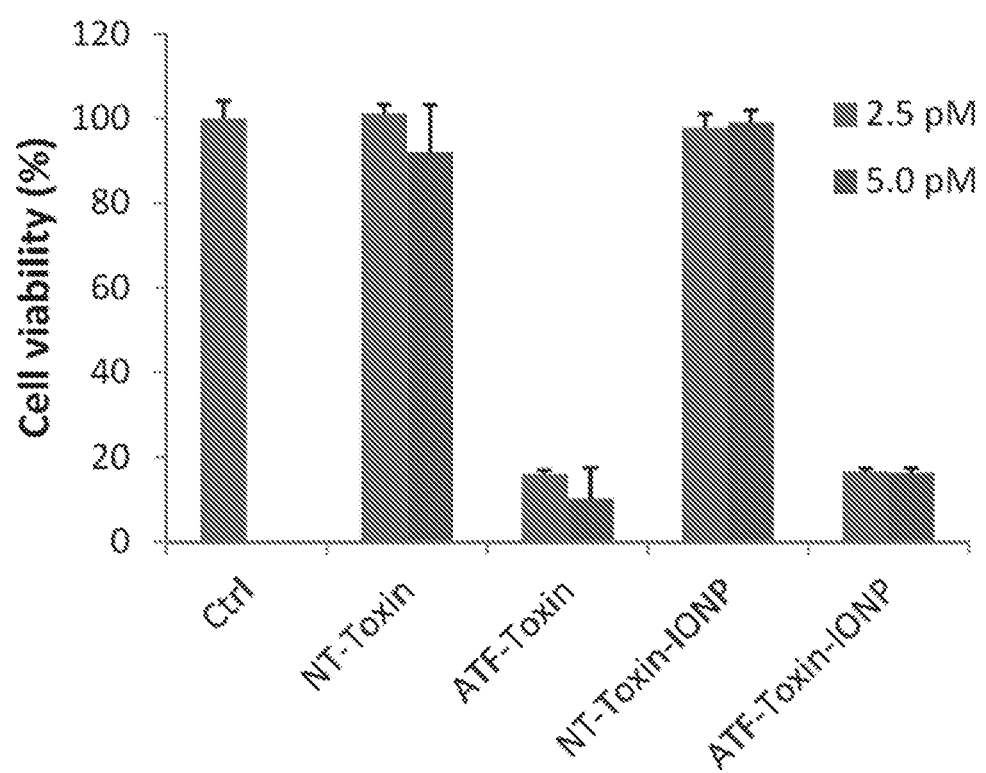
FIG. 4 shows data on in vitro cytotoxicity of unconjugated non-targeting PE38 (NT-toxin), ATF-PE38 (ATF-Toxin) and their related IONP conjugates. Preliminary breast cancer cells were derived from human breast PDX tumors.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

The term "nanoparticle" refers to a molecular conglomerate of about between 1 and 1000 nm in diameter. One more molecules or biomolecules linked to the nanoparticle typically refers to covalently attaching the molecules or biomolecules to a polymer based exterior or coating. Within certain embodiment, the compositions and methods disclosed herein may be utilized with a variety of polymer coated particle such as, e.g., quantum dots (QDs), metal particles, gold, silver, iron, and iron-oxide nanoparticles (IONPs).

An "isolated" peptide refers one that its sequence was synthesized chemically or by recombinant techniques and purified/isolated after synthesis. The peptide sequence is not purified from naturally occurring environment but may be derived from genetically modified cells or plants or bacterial expression systems.

A "specific binding" refers to binding by molecules, such as polynucleotides, antibodies, and other ligands, that are able to bind to or recognize a binding partner (or a limited number of binding partners) to a substantially higher degree than to other, similar biological entities.

A "subject" is defined to include any living animal or human. The term "non-human animal" includes all vertebrates, e.g., mammals and non-mammals, such as non-human primates, sheep, dog, cow, chickens, amphibians, reptiles, etc. A subject or non-human animal is "treated" if one or more beneficial or desired results, including desirably clinical results, are obtained. For purposes of this disclosure, beneficial or desired clinical results include, but are not limited to, one or more of the following: decreasing one or more symptoms resulting from the disease, increasing the quality of life of those suffering from the disease, decreasing the dose of other medications required to treat the disease, delaying the progression of the disease, and/or prolonging survival of individuals.

A "nucleic acid," or "oligonucleotide," is defined as a polymer of nucleotides. As used herein, a "nucleotide" is given its ordinary meaning as used in the art, i.e., a molecule comprising a sugar moiety, a phosphate group, and a base (usually nitrogenous). Typically, the nucleotide comprises one or more bases connected to a sugar-phosphate backbone (a base connected only to a sugar moiety, without the phosphate group, is a "nucleoside"). The sugars within the nucleotide can be, for example, ribose sugars (a "ribonucleic acid," or "RNA"), or deoxyribose sugars (a "deoxyribonucleic acid," or "DNA"). In some cases, the polymer can comprise both ribose and deoxyribose sugars. Examples of bases include, but are not limited to, the naturally-occurring bases (e.g., adenosine or "A," thymidine or "T," guanosine or "G," cytidine or "C," or uridine or "U"). In some cases, the polymer can also comprise nucleoside analogs (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, $N^1$-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, 6-O-methylguanine, 2-thiocytidine, etc.), chemically or biologically modified bases (e.g., methylated bases), intercalated bases, modified sugars (e.g., 2'-fluororibose, 2'-aminoribose, 2'-azidoribose, 2'-O-methylribose, L-enantiomeric nucleosides arabinose, hexose, etc.), modified phosphate moieties (e.g., phosphorothioates or 5'-N-phosphoramidite linkages), and/or other naturally and non-naturally occurring bases substitutable into the polymer, including substituted and unsubstituted aromatic moieties. Other suitable base and/or polymer modifications are well-known to those of skill in the art. In some cases, the polynucleotide can include DNA, RNA, modified DNA, modified RNA, antisense oligonucleotides, expression plasmid systems, nucleotides, modified nucleotides, nucleosides, modified nucleosides, intact genes, or combinations thereof. Other examples of polynucleotides include interfering RNA, natural or unnatural siRNAs, shRNAs, microRNAs, ribozymes, DNA plasmids, antisense oligonucleotides, randomized oligonucleotides, or ribozymes. A nucleic acid sequence may be composed of DNA nucleotides, RNA nucleotides or a combination of both types and may include natural nucleotides, chemically modified nucleotides and synthetic nucleotides.

"Amino acid sequence" is defined as a sequence composed of any one of the 20 naturally appearing amino acids, amino acids which have been chemically modified, or composed of synthetic amino acids. The terms "protein" and "peptide" refer to compounds comprising amino acids joined via peptide bonds and are used interchangeably. As used herein, where "amino acid sequence" is recited herein to refer to an amino acid sequence of a protein molecule. An "amino acid sequence" can be deduced from the nucleic acid sequence encoding the protein.

Sequence "identity" refers to the number of matching residues (expressed as a percentage) in a sequence alignment between two sequences of the alignment. As used herein, percentage identity of an alignment is calculated using the number of identical positions divided by the greater of the shortest sequence or the number of equivalent positions excluding overhangs wherein internal gaps are counted as an equivalent position. For example the polypeptides GGGGGG and GGGGT have a sequence identity of 4 out of 5 or 80%. For example, the polypeptides GGGPPP and GGGAPPP have a sequence identity of 6 out of 7 or 85%.

Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q.

The terms "variant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Certain variants have less than 10%, and preferably less than 5%, and still more preferably less than 2% changes (whether substitutions, deletions, and so on).

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. Common expression systems, for the expression of a protein coded for by foreign DNA carried by the vector and introduced to the host cell, include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective, rat YB2/3HL.P2.G11.16Ag.20 cell (ATCC CRL1662, hereinafter referred to as "YB2/0 cell"), and the like.

In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

In certain embodiments, the disclosure relates to recombinant peptides comprising sequences disclosed herein or variants or fusions thereof wherein the amino terminal end or the carbon terminal end of the amino acid sequence are optionally attached to a heterologous amino acid sequence, label, or reporter molecule.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}$S or $^{131}$I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the disclosure relates to the recombinant vectors comprising a nucleic acid encoding a peptide disclosed herein or fusion protein thereof and optionally a selectable marker. A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: amp$^r$, cam$^r$, tet$^r$, blasticidin$^r$, neo$^r$, hyg$^r$, abx$^r$, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferaseI (galT), feedback-insensitive a subunit of anthranilate synthase (OASA1D), 2-deoxyglucose (2-DOGR), benzyladenine-N-3-glucuronide, E. coli threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

In certain embodiments, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

"Radiation therapy" is defined as a cancer treatment that uses high-energy x-rays or other types of radiation to kill cancer cells or keep them from growing. There are two types of radiation therapy. External radiation therapy, which uses a machine outside the body to send radiation to the cancer. Internal radiation therapy uses a radioactive substance sealed in needles, seeds, wires, or catheters that are placed directly into or near the cancer. The way the radiation therapy is administer is directly dependent on the type and stage of the cancer.

"Chemoradiation therapy" is defined as a therapy that combines chemotherapy and radiation therapy to increase the effects of both.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others. The cancer to be treated in the context of the present disclosure may be any type of cancer or tumor.

With regard to fusions proteins disclosed herein, a "toxin" refers to a polypeptide that impedes or slows the growth of a cancerous cell or tumor. PE38 is toxin which is a truncated portion of Pseudomonas aeruginosa exotoxin A (PE) having the following amino acid sequence (SEQ ID NO: 11) EGGSLAALTAHQACHLPLETFTRHRQPRGWEQLE-QCGYPVQRLVALYLAARLSWNQV DQVIRNAL-ASPGSGGDLGEAIREQPEQARLALTLAAAESER-FVRQGTGNDEAGAANGPA DSGDALLERNYPTGAE-FLGDGGDVSFSTRGTQNWTVERLLQAHRQLEERG-YVFVGYHG TFLEAAQSIVFGGVRARSQDL-DAIWRGFYIAGDPALAYGYAQDQEPDARGRIRN-GALLR VYVPRSSLPGFYRTSLTLAAPEAAGEVER-LIGHPLPLRLDAITGPEEEGGRLETILGWPLA ERTVVIPSAIPTDPRNVGGDLDPSSIPDKEQAIS- ALPDYASQPG. In certain embodiments, the disclosure is not limited to the PE38 toxin as other toxic peptides are contemplated.

Nanoparticles

This disclosure relates to nanoparticles comprising a toxin or a fusion protein that acts as a targeting moiety and a toxin. In certain embodiments, the fusion protein comprises SEQ ID NO: 1, 3, 4, 5, or variants thereof. When reference is made to a metal particle or nanoparticle comprising a peptide or toxin, it is understood that the peptide, fusion protein, and/or toxin is bound to the particle through a polymer coating, either through covalent bonds or other binding interactions, e.g., hydrophobic or hydrophilic binding or chelating interactions.

Within certain embodiment, the compositions and methods disclosed herein may be utilized with a variety of polymer coated particle such as, e.g., quantum dots (QDs), metal particles, gold, silver, iron, and iron-oxide nanoparticles (IONPs). IONPs are typically prepared with a mean particle diameter of 4-100 nm. IONPs may be prepared by aging a stoichiometric mixture of ferrous and ferric salts in aqueous media under basic conditions. Control over particle size (2-20 nm) and shape is provided by adjusting the pH, ionic strength and the concentration of the growth solution. The nanoparticles can be functionalized in situ using additives such as organic compounds (e.g. sodium citric) or polymers (e.g. dextran, polyvinyl alcohol). Other metals such as gold, cobalt, nickel, and manganese may be incorporated into the material.

High-temperature decomposition of $Fe(CO)_5$ in organic solvents is another way to prepare IONPs. Size (3-19 nm) can be varied using alternative temperatures. Flame spray pyrolysis yields a range of magnetite, maghemite and wustite (FeO) particles IONPs. Iron precursor such as $Fe(CO)_5$ and $Fe(NO_3)_3$ may be used. Flame spray pyrolysis can be used to produce different nanoparticles ($TiO_2$, ZrO2, silica, etc.) as well as hybrid particles (e.g. silica-IONPs).

Hydroxyl groups on the IONP provide a place for synthetic attachment of different functional groups. A range of chemistries can be used to stabilize metal nanoparticles, exploiting electrostatic, hydrophobic, chelating and covalent interactions. Carboxylic acid groups can interact with the surface of IONPs by coordination processes. IONP synthesis in organic solvents is typically conducted in oleic acid. A polymer coating on the IONPs is preferred. Polymer attachment to the IONP surface by an initiator fixed to the surface of the IONPs and the polymer is grown from the surface. Alternatively, a functional, pre-formed polymer is grafted onto IONPs in situ. Copolymers with hydrophobic groups, carboxylic acid groups, polyethylene glycols, or amine groups are contemplated. Polymers with a hydrophilic block and a hydrophobic block are contemplated. See Yang et al., Clin Cancer Res, 2009 15:4722; Lin et al., Small, 2008, 4(3):334-341; Yu et a., Nanotechnology, 2006, 17:4483-4487; Park et al., J. Mater. Chem., 2009, 19, 6412-6417; Boyer et al. NPG Asia Mater., 2010, 2(1):23-30, Kim et al., Nanotechnology, 2011, 22, 155101; all hereby incorporated by reference in their entirety.

Conjugating molecules or polypeptides to the polymers can be accomplished using a variety of methods. Typically, primary amine containing compounds and proteins may be conjugated to the carboxylic acid groups on the polymer mediated by a coupling reagent such as EDAC. See Yang et al., Small, 2009, 5(2):235-43, hereby incorporated by reference in its entirety. Other coupling methods are contemplated, e.g., poly-histidine sequence may be recombinantly incorporated into a polypeptide sequence of the targeting moiety. A poly-histidine chelating agent may be coupled to the polymer surface, e.g., NTA-Ni or NTA-Cu. Mixing the histidine tagged polypeptide sequence attaches it to the polymer surface linked through the chelating agent NTA. The avidin/streptavidin-biotin interactions may be used, e.g., biotin may be coupled to the polymer surface and streptavidin may be expressed as a chimera with the targeting moiety.

In certain embodiments, a fusion protein disclosed herein comprises an amino-terminal fragment (ATF) of uPA, e.g., amino terminal fragment of human uPA and a toxin.

In certain embodiments, the ATF-uPA comprises or consist of ATF, 135 aa (17 kDa) (SEQ ID NO: 6) SNELHQVPSNCD-CLNGGTCVSNKYFSNIHWCNCPKKFGGQHCEIDK-SKTCYEGNGHFY RGKASTDTMGRPCLPWNSATV-LQQTYHAHRS-DALQLGLGKHNYCRNPDNRRRPWCY VQVGLKPLVQECMVHDCADGK.

In certain embodiments, the ATF-uPA comprises or consist of ATF, 68 aa of human uPA (SEQ ID NO: 7)
SNELHQVPSNCDCLNGGTCVSNKYFSNIHWCNCPKKFGGQHCEIDKSKTCY
EGNGHFYRGKASTDTMG.

In certain embodiments, the ATF-uPA comprises or consist of ATF, 39 (aa, 10-47)

(SEQ ID NO: 8)
NCDCLNGGTCVSNKYFSNIHWCNCPKKFGGQHCEIDKSK.

In the context of these sequences, term "comprise" refers to an ATF-uPA that may contain more of the ATF-uPA sequence or other peptide, and the term "consist of" refers to the sequence not having additional amino acids on the N-terminal or C-terminal ends that match human ATF-uPA, but may contain other peptide sequences.

In certain embodiments, the fusion protein disclosed herein comprises a peptide that binds EGFR.

ATF may be produced from *E. coli* BL21 bacterial expression system using a pET20a plasmid (Invitrogen, Grand Island, N.Y.) containing the ATF cDNA sequence. Urokinase plasminogen activator (uPA) is a serine protease that regulates multiple pathways involved in matrix degradation, cell motility, metastasis and angiogenesis. Interaction of the N-terminal growth factor domain of uPA with its cellular receptor (uPAR) results in the conversion of the plasminogen to a serine protease, which is a central regulator of the activation of other proteases including the matrix metalloproteinases (MMPs). Studies have shown that the uPA/uPAR complex controls the motility of both tumor and endothelial cells. In addition to its role in activation of the process for degradation of extracellular matrix, uPAR also activates α5β1 integrin and ERK signaling through interaction with EGFR and induces cell proliferation. Additionally, the uPA/uPAR complex can bind to the matrix protein, vitronectin, in association with transmembrane integrins, and activate intracellular signaling molecules such as the protein kinases, promoting cell adhesion, proliferation, and migration.

The uPAR-binding domain of uPA is located to the amino-terminal fragment (ATF) of uPA. Studies have shown that ATF is a potent uPA binding antagonist to its high affinity receptor (uPAR) at the surface of both tumor and endothelial cells. Systemic or local delivery of a non-catalytic amino-terminal fragment (ATF) of uPA (residues 1-135) using an adenoviral vector or conjugated peptides prevents the formation of the uPA/uPAR complex, thus inhibiting tumor growth and angiogenesis. Yang et al., Clin Cancer Res., 2009, 15(14):4722-32, hereby incorporated by reference in its entirety, discuss the preparation of targeted iron oxide nanoparticle using a recombinant peptide containing the amino-terminal fragment of urokinase-type plasminogen activator (uPA) conjugated to magnetic iron oxide nanoparticles amino-terminal fragment conjugated-iron oxide nanoparticle (ATF-IONP). This nanoparticle targets uPA receptor, which is overexpressed in breast cancer tissues.

In certain embodiments, the peptide that binds EGFR may be ScFvEGFR (SEQ ID NO: 9)
TSEIVMTQSPATLSLSPGERATLSCRASQSVSSYLAWYQQKPGQAPRLLIY

DASNRATGIPARFSGSGSGTDFTLTISRLEPEDFAVYYCQQYGSSPITFGQ

GTRLEIKRS.

In certain embodiments, nanoparticles disclosed herein comprise a fusion protein disclosed herein that function as a targeting moiety and a toxin. In certain embodiments, the nanoparticles further comprise a second targeting moiety such as human IGF1

(SEQ ID NO: 10)
MGKISSLPTQLFKCCFCDFLKVKMHTMSSSHLFYLALCLLTFTSSATAGP

ETLCGAELVDALQFVCGDRGFYFNKPTGYGSSSRRAPQTGIVDECCFRSC

DLRRLEMYCAPLKPAKSARSVRAQRHTDMPKTQKEVHLKNASRGSAGNKN

YRM.

In certain embodiments, the second targeting moiety is a moiety that binds EGFR. The human epidermal growth factor receptor (EGFR) family includes EGFR (HER-1), EGFR-2 (HER-2), EGFR-3 (Her-3) and EGFR 4 (HER-4). The ligands that bind to EGFRs are divided into EGFR-like ligands such as EGF and TGF-α, and the hereguilins. These ligands bind to EGFR monomers to promoter receptor dimerization and oligomerization that ultimately results in the activation of the EGFR signaling pathway. This EGFR signaling pathway plays a role in the regulation of cell proliferation, survival and differentiation.

Human breast carcinomas express high levels of the EGF receptors. Overexpression of this receptor has been associated with highly aggressive breast cancer types and a poor response to therapeutic agents. Prior preclinical and clinical studies have shown that blocking the EGFR via monoclonal antibodies or inhibition of EGFR tyrosine kinase with small molecule inhibitors inhibits the growth of breast cancers and sensitize chemotherapy responses. Single-chain antibodies to EGFR that contain the specific EGFR binding region but lack the Fc region have been isolated from human scFv phage display libraries. Yang et al., Small, 2009, 5(2):235-43, hereby incorporated by reference in its entirety, discuss the preparation of EGFR targeted nanoparticles conjugating a single-chain anti-EGFR antibody (ScFvEGFR).

Iron oxide nanoparticles conjugated to a purified antibody that selectively binds to the epidermal growth factor receptor (EGFR) deletion mutant (EGFRvIII) present on human glioblastoma multiforme (GBM) cells were used for therapeutic targeting and MM contrast enhancement of experimental glioblastoma, both in vitro and in vivo, after convection-enhanced delivery (CED). See Hadjipanayis et al., Cancer Res, 2010, 70:6303, hereby incorporated by reference in its entirety. In certain embodiments, the disclosure relates to targeting moiety that is an antibody or antibody mimetic to EGFR or EGFRvIII for use in treating glioblastoma multiforme.

In certain embodiments, the second targeting moiety is a monoclonal antibody-610 that targets a surface antigen for use in treating colon carcinoma. See Cerdan et al., Magn Reson Med, 1989, 12:151-63 1989, hereby incorporated by reference in its entirety.

In certain embodiments, the second targeting moiety is an antibody to carcinoembryonic antigen (CEA) that targets CEA for use in treating colon tumors. See Tiefenauer et al., Magn Reson Imaging, 1996, 14:391-402, hereby incorporated by reference in its entirety.

In certain embodiments, the second targeting moiety is a monoclonal antibody L6 that targets a surface antigen for use in treating intracranial tumor. See Remsen et al., Am J Neuroradiol, 1996, 17:411-18, hereby incorporated by reference in its entirety.

In certain embodiments, the second targeting moiety is transferrin that targets transferrin receptor for use in treating carcinoma. See Kresse et al., Magn Reson Med, 1998, 40:236-42, hereby incorporated by reference in its entirety.

In certain embodiments, the second targeting moiety is a monoclonal antibody to Her-2, e.g., Herceptin, which targets Her-2 receptors for use in treating breast cancer. See Lee et al., Nat Med, 2007, 13:95-9; Artemov et al., Magn Reson Med, 2003, 49:403-8; and Huh et al., J Am Chem Soc, 2005, 127:12387-91, all hereby incorporated by reference in their entirety.

In certain embodiments, the second targeting moiety is the EPPT peptide that targets underglycosylated mucin-1 antigen (uMUC-1) for use in treating breast, colon, pancreas, and lung cancer. See Moore et al., Cancer Res, 2004, 64:1821-7, hereby incorporated by reference in its entirety.

In certain embodiments, the second targeting moiety is folic acid that targets folate receptor for use in treating mouth carcinoma and cervical cancer. See Chen et al., PDA J Pharm Sci Technol, 2007, 61:303-13; Sun et al., Small, 2006, 4:372-9; and Sonvico et al., Bioconjug Chem, 2005, 16:1181-8, all hereby incorporated by reference in their entirety.

In certain embodiments, the second targeting moiety is methotrexate that targets folate receptor for use in treating cervical cancer. See Kohler et al., Langmuir, 2005, 21:8858-64, hereby incorporated by reference in its entirety.

In certain embodiments, the second targeting moiety is a monoclonal antibody A7 that targets colorectal tumor antigen for use in treating colorectal carcinoma. See Toma et al., Br J Cancer, 2005, 93:131-6, hereby incorporated by reference in its entirety.

In certain embodiments, the second targeting moiety is chlorotoxin peptide that targets membrane-bound matrix-metalloproteinase-2 (MMP-2) for use in treating glioma. See Veiseh et al., Nano Lett, 2005, 5:1003-8, hereby incorporated by reference in its entirety.

In certain embodiments, the second targeting moiety is F3 peptide that targets surface-localized tumor vasculature for use in treating glioma. See Reddy et al., Clin Cancer Res, 2006, 12:6677-86, hereby incorporated by reference in its entirety.

In certain embodiments, the second targeting moiety is RGD or RGD4C that targets integrins for for use in treating melanoma and epidermoid carcinoma. See Zhang et al., Cancer Res, 2007, 67:1555-62 and Uchida et al., J Am Chem Soc, 2006, 128:16626-33, both hereby incorporated by reference in their entirety.

In certain embodiments, the second targeting moiety is luteinizing hormone releasing hormone (LHRH) that targets LHRH receptor for use in treating breast cancer. See Leuschner et al., Breast Cancer Res Treat, 2006, 99:163-76, hereby incorporated by reference in its entirety.

In certain embodiments, the second targeting moiety is CREKA peptide that targets clotted plasma proteins for use in treating breast cancer. See Simberg et al., Proc Natl Acad Sci USA, 2007, 104:932-6, hereby incorporated by reference in its entirety.

In certain embodiments, the second targeting moiety is an antibody to prostate specific membrane antigen (PSMA) that targets PSMA for use in treating prostate cancer. See Serda et al., Mol Imaging, 2007, 6:277-88, hereby incorporated by reference in its entirety.

In certain embodiments, the disclosure relates to multifunctional nanoparticles comprising a targeting peptide disclosed herein, the nanoparticle, and a cargo. The nanoparticles can be either Quantum Dots (QDs) or gold nanoparticles that can be imaged optically or iron oxide nanoparticles (IONPs) that can be imaged via MRI. In certain embodiments the cargo is either a DNA cassette coding for a siRNA against an oncogene or survival factor, a chemotherapy drug or both.

Since siRNA is expressed from a RNA polymerase III (e.g., U6 or H1) promoter, a short hairpin siRNA (shRNA) gene may be cloned into expression vectors containing a polymerase III promoter to produce shRNAs from plasmid or viral vectors following transfecting into cells. See Brummelkamp et al., Science, 2002, 296, 550-553; Miyagishi & Taira, Nat. Biotechnol, 2002, 20, 497-500; McAnuff et al, J. Pharm. Sci. 2007, 96, 2922-2930; Bot et al., Blood, 2005, 106, 1147-1153. The shRNAs are further processed into siRNAs by a cellular endoribonuclease. DNA cassettes expressing shRNA containing a U6 promoter and a shRNA gene can be synthesized by a two-step PCR amplification protocol. See Castanotto et al., RNA, 2002, 8, 1454-1460 and Gou et al., FEBS Lett., 2003, 548, 113-118.

In certain embodiments provided herein is a particle that contains a polymer-coated nanoparticle core, e.g., a fluorescent quantum dot (QD) or MM contrast enhancing magnetic iron oxide nanoparticle (IONP), conjugated with about 10 to 20 DNA nanocassettes that contain a U6 promoter and a shRNA gene for in vivo siRNA gene expression following intracellular delivery. The nanoparticle is conjugated to a targeting peptide disclosed herein typically the amino terminal fragment (ATF) of the urokinase plasminogen activator (uPA), which targets its cellular receptor, uPAR. This receptor is highly expressed in tumors, angiogenic endothelial, and stromal cells in many types of human cancers. See Nielsen et al., Int. J. Cancer 2007, 120, 2086-2095; Blasi & Carmeliet, Nat. Rev. Mol. Cell Biol. 2002, 3, 932-943; Pyke et al., Cancer Res, 1993, 53, 1911-1915.

In certain embodiments, the disclosure relates to particles comprising a core coated with a polymer, wherein the polymer is conjugated to a targeting moiety, a lysosomally degradable moiety, and a therapeutic agent such as gemcitabine, doxorubicin, cytosine arabinoside, mitomycin, or any therapeutic agent with that an amine side group. In certain embodiments, the therapeutic agent is cisplatin, camptothecin or derivative such as 7-ethyl-10-hydroxycamptothecin (SN-38) or 7-ethyl-10-[4-(1-piperidino)-1-piperidino] carbonyloxy camptothecin (CPT-11). In certain embodiments, the particle is a metal nanoparticle or metal oxide nanoparticle, such as an iron oxide nanoparticle or elemental iron core nanoparticle with an oxide coat, or a quantum dot, e.g., those with a diameter of between about 5 to 200 nm or 10 to 100 nm. In certain embodiments, the lysosomally degradable moiety is the polypeptide GFLG (SEQ ID NO: 12) linked to the therapeutic agent. In certain embodiments, the disclosure relates to compositions comprising a polymer conjugated to a targeting moiety, lysosomally degradable moiety, and a therapeutic agent which are described herein. In one example, the lysosomally degradable moiety linked to the therapeutic agent is of the formula:

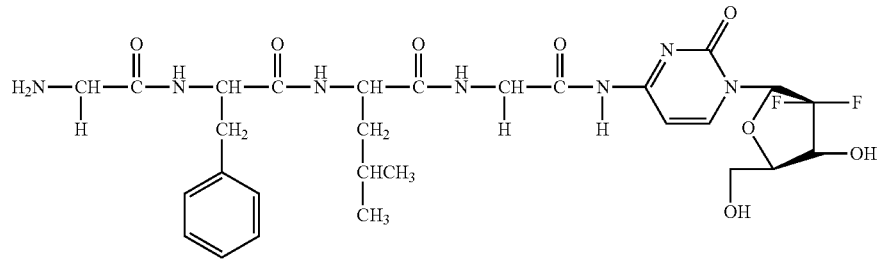

or salts or derivatives thereof optionally substituted with one or more substituents. In certain embodiments, the polymer is an amphiphilic polymer comprising a hydrophobic section further comprising a hydrophobic chemotherapeutic agent.

In certain embodiments, nanoparticles are coated with a siloxane polymer such as PEG-b-AGE polymer. Li et al report PEG-b-AGE polymer coated magnetic nanoparticle probes with facile functionalization and anti-fouling properties for reducing non-specific uptake and improving biomarker targeting. J. Mater. Chem. B, 2015, 3, 3591-3603

In certain embodiments, the particle further comprises a fluorescent dye, e.g., a (3,3-dimethyl-indol-1-ium-1-yl)-N-alkylsulfonate dye or salt thereof such as one of the formula:

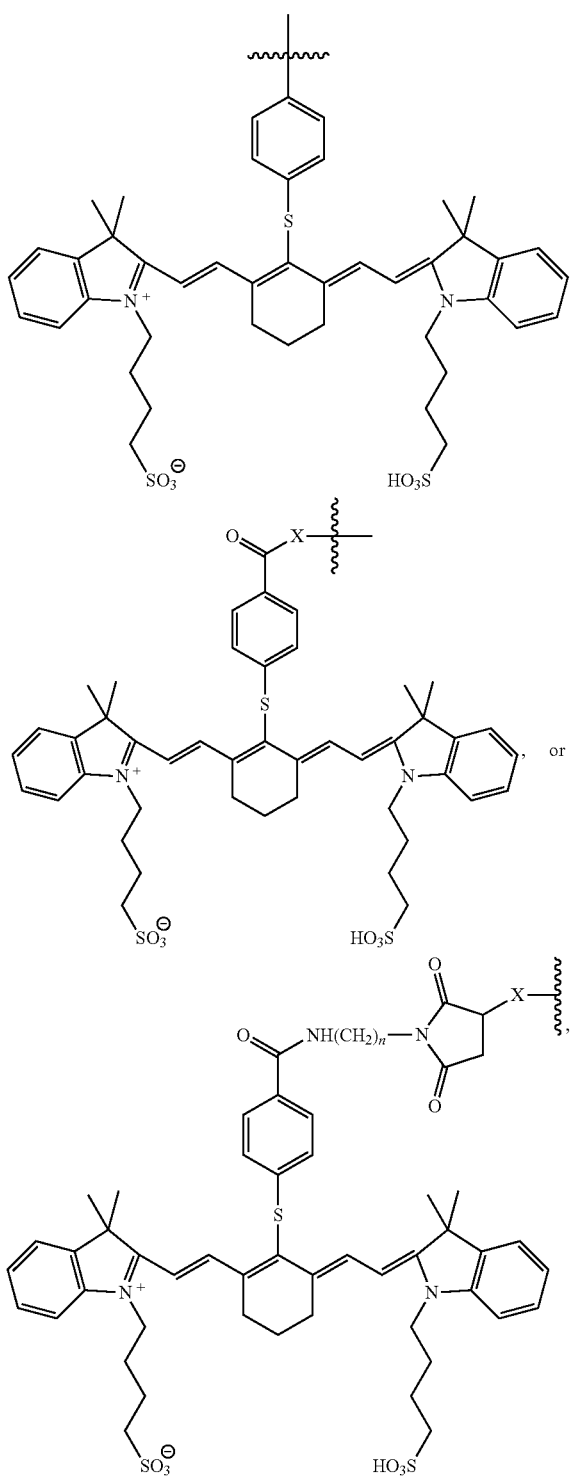

or salts or derivatives thereof optionally substituted with one or more substituents wherein X is S or NH and n is 2 to 22 or n is 4 to 22. In certain embodiments, the dye is conjugated to the free thiol group on cysteine or free amino group of the peptides or proteins.

Methods of Use

In certain embodiments, this disclosure relates to a method of treating cancer comprising administering an effective amount of a nanoparticle comprising a fusion protein disclosed herein or a fusion protein disclosed herein, to a subject in need thereof.

In certain embodiments, this disclosure relates to a method of treating cancer comprising administering an effective amount of a nanoparticle comprising a fusion protein comprising SEQ ID NO: 1, 3, 4, 5, or variants to a subject in need thereof.

In certain embodiments, this disclosure relates to a method of treating cancer comprising administering an effective amount of a fusion protein comprising SEQ ID NO: 1, 3, 4, 5, or variants to a subject in need thereof. In certain embodiments, the fusion protein may be administered in combination with a nanoparticle comprising an amino-terminal fragment (ATF) of uPA or the fusion protein may be incorporated into the nanoparticle.

In certain embodiments, the disclosure contemplates a combination chemotherapy comprising the administration of a first agent in combination with a second agent, wherein the first agent is a nanoparticle comprising a fusion protein having SEQ ID NO: 1, 3, 4, 5 or variant thereof, wherein the second agent is a nanoparticle comprising a an amino-terminal fragment (ATF) of uPA and a chemotherapy agent attached to the nanoparticle or the chemotherapy agent is encapsulated by a polymer around the core of the particle.

In certain embodiments, the cancer overexpresses a receptor of a targeting molecule in tumor cells, tumor endothelial cells, or tumor stromal fibroblasts compared to noncancerous tissue of an organ containing the cancerous tumor. In certain embodiments, the targeting molecule is an antibody or fragment, antibody mimetic, inhibitor, or aptamer targeting a protein or glycoprotein expressed on the surface of a cancerous cell. In certain embodiments, the cancer overexpress uPAR, IGF1R, EGFR, or HER-2. In certain embodiments, the cancer is selected from pancreatic cancer, breast cancer, prostate cancer, lung cancer, skin cancer, bladder cancer, brain cancer, colon cancer, rectal cancer, kidney cancer, endometrial cancer, and thyroid cancer.

In certain embodiments, the cancer is selected from carcinoma, lymphoma, blastoma, sarcoma, and leukemia, non-small cell lung, squamous cell, small-cell lung, peritoneum, hepatocellular, gastrointestinal, pancreatic, glioma, cervical, ovarian, liver, bladder, hepatoma, breast, colon, colorectal, endometrial or uterine, salivary gland, kidney, liver, prostate, vulval, thyroid, hepatic, leukemia and other lymphoproliferative disorders, and various types of head and neck. In certain embodiments, the cancer can be a primary or metastatic tumors.

In further embodiments, this disclosure relates to methods of treating cancer further comprising administering a particle disclosed herein comprising a second chemotherapy agent or administering a second chemotherapy to the subject separate from any chemotherapy agent contained in or attached to the particle and/or the surrounding polymer. In certain embodiments, particles disclosed herein are administered an effective amount to treat a subject diagnosed with cancer or a cancerous tumor. In certain embodiments, the particles disclosed herein are administered in combination with a second anti-cancer agent such as, but not limited to, anti-CTLA-4 antibodies, anti-PD-1 antibodies, anti-PD-L1 antibodies, nivolumab, pembrolizumab, ipilimumab, tremelimumab, bevacizumab, gefitinib, erlotinib, temozolomide, docetaxel, cisplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vincristine, vinblastine, vindesine, vinorelbine taxol, taxotere, etoposide, teniposide, amsacrine, topotecan, camptothecin, bortezomib, anagrelide, tamoxifen, toremifene, raloxifene, droloxifene, iodoxyfene fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, and/or lenalidomide or combinations thereof.

In certain embodiments, the methods disclosed herein may be used in combination with radiation and chemoradiation therapy.

In certain embodiments, this disclosure relates to a method for cancer diagnosis comprising administering an effective amount of a fusion protein disclosed herein or nanoparticle disclosed herein to a subject in need thereof and detecting the particle about the area of a cancerous cell or tumor.

Also contemplated are malignancies located in the colon, abdomen, bone, breast, digestive system, liver, pancreas, peritoneum, endocrine glands (adrenal, parathyroid, hypophysis, testicles, ovaries, thymus, thyroid), eye, head and neck, nervous system (central and peripheral), lymphatic system, pelvis, skin, soft tissue, spleen, thorax and genito-urinary apparatus and, more particularly, childhood acute lymphoblastic leukemia, acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignant tumors, anal cancer, astrocytoma, cancer of the biliary tract, cancer of the bladder, bone cancer, brain stem glioma, brain tumors, breast cancer, cancer of the renal pelvis and ureter, primary central nervous system lymphoma, central nervous system lymphoma, cerebellar astrocytoma, brain astrocytoma, cancer of the cervix, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood brain astrocytoma, childhood extracranial germ cell tumors, childhood Hodgkin's disease, childhood Hodgkin's lymphoma, childhood visual pathway and hypothalamic glioma, childhood lymphoblastic leukemia, childhood medulloblastoma, childhood non-Hodgkin's lymphoma, childhood supratentorial primitive neuroectodermal and pineal tumors, childhood primary liver cancer, childhood rhabdomyosarcoma, childhood soft tissue sarcoma, childhood visual pathway and hypothalamic glioma, chronic lymphocytic leukemia, chronic myeloid leukemia, cancer of the colon, cutaneous T-cell lymphoma, endocrine pancreatic islet cells carcinoma, endometrial cancer, ependymoma, epithelial cancer, cancer of the esophagus, Ewing's sarcoma and related tumors, cancer of the exocrine pancreas, extracranial germ cell tumor, extragonadal germ cell tumor, extrahepatic biliary tract cancer, cancer of the eye, breast cancer in women, Gaucher's disease, cancer of the gallbladder, gastric cancer, gastrointestinal carcinoid tumor, gastrointestinal tumors, germ cell tumors, gestational trophoblastic tumor, tricoleukemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, cancer of kidney, cancer of the larynx, cancer of the lip and mouth, cancer of the liver, cancer of the lung, lymphoproliferative disorders, macroglobulinemia, breast cancer in men, malignant mesothelioma, malignant thymoma, medulloblastoma, melanoma, mesothelioma, occult primary metastatic squamous neck cancer, primary metastatic squamous neck cancer, metastatic squamous neck cancer, multiple myeloma, multiple myeloma/plasmatic cell neoplasia, myelodysplastic syndrome, myelogenous leukemia, myeloid leukemia, myeloproliferative disorders, paranasal sinus and nasal cavity cancer, nasopharyngeal cancer, neuroblastoma, non-Hodgkin's lymphoma during pregnancy, non-melanoma skin cancer, non-small cell lung cancer, metastatic squamous neck cancer with occult primary, buccopharyngeal cancer, malignant fibrous histiocytoma, malignant fibrous osteosarcoma/histiocytoma of the bone, epithelial ovarian cancer, ovarian germ cell tumor, ovarian low malignant potential tumor, pancreatic cancer, paraproteinemias, purpura, parathyroid cancer, cancer of the penis, pheochromocytoma, hypophysis tumor, neoplasia of plasmatic cells/multiple myeloma, primary central nervous system lymphoma, primary liver cancer, prostate cancer, rectal cancer, renal cell cancer, cancer of the renal pelvis and ureter, retinoblastoma, rhabdomyosarcoma, cancer of the salivary glands, sarcoidosis, sarcomas, skin cancer, small cell lung cancer, small intestine cancer, soft tissue sarcoma, squamous neck cancer, stomach cancer, pineal and supratentorial primitive neuroectodermal tumors, T-cell lymphoma, testicular cancer, thymoma, thyroid cancer, transitional cell cancer of the renal pelvis and ureter, transitional renal pelvis and ureter cancer, trophoblastic tumors, cell cancer of the renal pelvis and ureter, cancer of the urethra, cancer of the uterus, uterine sarcoma, vaginal cancer, optic pathway and hypothalamic glioma, cancer of the vulva, Waldenstrom's macroglobulinemia, Wilms' tumor and any other hyperproliferative disease, as well as neoplasia, located in the system of a previously mentioned organ.

A "chemotherapy agent," "chemotherapeutic," "anti-cancer agent" or the like, refer to molecules that are recognized to aid in the treatment of a cancer. Contemplated examples include the following molecules or derivatives such as temozolomide, carmustine, bevacizumab, procarbazine, lomustine, vincristine, gefitinib, erlotinib, cisplatin, carboplatin, oxaliplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vinblastine, vindesine, vinorelbine, paclitaxel, taxol, docetaxel, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, azacitidine, azathioprine, capecitabine, chlorambucil, cyclophosphamide, cytarabine, daunorubicin, doxifluridine, epothilone, irinotecan, mechlorethamine, mercaptopurine, mitoxantrone, pemetrexed, tioguanine, valrubicin and/or lenalidomide or combinations thereof such as, cyclophosphamide, methotrexate, 5-fluorouracil (CMF); doxorubicin, cyclophosphamide (AC); mustine, vincristine, procarbazine, prednisolone (MOPP); adriamycin, bleomycin, vinblastine, dacarbazine (ABVD); cyclophosphamide, doxorubicin, vincristine, prednisolone (CHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

In certain embodiments, the disclosure relates to methods of optical and MM imaging the nanoparticle in tumors. 3D-MM enables monitoring of intratumoral distribution of nanoparticles and tumor responses to therapeutics contained on or in the nanoparticles.

In certain embodiments, the disclosure relates to nanoparticles coated with amphiphilic polymers or PEG-b-AGE polymers conjugated with molecules useful for targeting tumors, monitoring the location of the nanoparticles administered to a subject by MRI, and viewing the presence of the nanoparticles during optical image-guided surgery.

In certain embodiments, the disclosure relates to uses of particles disclosed herein as a theranostics. Theranostics are therapeutics with physical properties that allows one to image molecular accumulation of the vehicles in vivo. Yang et al., WO/2007/018647, disclose binding and internalization of tumor targeted-iron oxide particles using MRI. See also Yang et al., J. Biomed. Nanotechnol., 2008, 4, 439-449. Lammers et al., Biomaterials, 2009, 30(2):3466-3475, disclose the simultaneous delivery of doxorubicin and gemcitabine to tumors in vivo using polymeric drug carriers.

In certain embodiments, the disclosure relates to methods comprising preoperatively administering a composition comprising nanoparticles disclosed herein and monitoring the location of the particles in the subject by detecting it by MRI (magnetic resonance imaging) in an area of the subject. In certain embodiments, the method further comprises the steps of operating on the subject in the area of detected particles, imaging dye identified tumors binding the targeting molecule, and surgically removing dye identified tumors or tissue.

In certain embodiments, the disclosure relates to methods comprising preoperatively administering cancer targeted nanoparticles conjugated to dyes disclosed herein to a subject, optically imaging a tumor that bind the nanoparticles intra-operatively, and removing tumors targeted with the nanoparticles.

In certain embodiments, the disclosure contemplates imaging and effecting cancer cell lysis or other cell lysis with particles using iron or iron oxide cores. See WO2009/120702.

In certain embodiments, the disclosure relates to targeting of cancer by local hyperthermia using composition and methods disclosed herein. Local hyperthermia can lead to induction of apoptosis, heat-shock protein release, and chemotherapy agent sensitivity of cancer cells by exposure of cancer cells containing particles with an iron or iron oxide core to an alternating magnetic fields (<1000 kHz) that are safe to normal cells.

In certain embodiments, the disclosure relates to methods for lysis of a cancer cells comprising, administering to a subject particles disclosed herein and adjusting magnetic fields proximate the subject to cause cell lysis of cancer cell that absorb the particles after administration. Typically, the magnetic field is an oscillating magnetic field and the particles are heated to at least 37° C. in vivo typically greater than 41° C.

Pharmaceutical Compositions

In certain embodiments, the disclosure relates to pharmaceutical compositions comprising particles disclosed herein and a pharmaceutically acceptable excipient. In certain embodiments, the composition is a pill or in a capsule or the composition is an aqueous buffer, e.g., a pH between 6 and 8. In certain embodiments, the pharmaceutically acceptable excipient is selected from a filler, glidant, binder, disintegrant, lubricant, and saccharide. Optionally, the pharmaceutical composition further comprises a second anticancer agent.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and viscoleo) and injectable organic esters such as ethyl oleate.

Prevention of the action of microorganisms may be controlled by addition of any of various antibacterial and antifungal agents, example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the particles may be admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar and as high molecular weight polyethylene glycols, and the like.

Solid dosage forms such as tablets, capsules, pills, and granules can be prepared with coatings and shells, such as enteric coatings and others well known in the art. They may contain opacifying agents, and can also be of such composition that they release the particles in a certain part of the intestinal tract in a delayed manner. Examples of embedding compositions which can be used are polymeric substances and waxes.

Liquid dosage forms for oral administration include pharmaceutically acceptable emulsions, solutions, suspensions, syrups, and elixirs. In addition to the particles, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, viscoleo, castor oil and sesame oil, glycerol, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents. Suspensions, in addition to the particles, may contain suspending agents, as for example, ethoxylated iso-stearyl alcohols, polyoxyethylene sorbitol and sorbitan esters, microcrystalline cellulose, aluminum metahydroxide, bentonite agar-agar and tragacanth, or mixtures of these substances, and the like.

Pharmaceutical compositions typically comprise an effective amount of particles and a suitable pharmaceutical acceptable carrier. The preparations can be prepared in a manner known per se, which usually involves mixing the particles according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

The pharmaceutical preparations of the disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, of the particles of the disclosure e.g., about 10, 25, 50, 100, 200, 300 or 400 mg per unit dosage.

The particles can be administered by a variety of routes including the oral, ocular, rectal, transdermal, subcutaneous, intravenous, intramuscular or intranasal routes, depending mainly on the specific preparation used. The particles will generally be administered in an "effective amount," by which it is meant any amount of particles that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the subject per day, more often between 0.1 and 500 mg, such as between 1 and 250 mg, for example about 5, 10, 20, 50, 100, 150, 200 or 250 mg, per kilogram body weight of the subject per day, which can be administered as a single daily dose, divided over one or more daily doses. The amount(s) to be administered, the route of administration and the further treatment regimen can be determined by the treating clinician, depending on factors such as the age, gender and general condition of the subject and the nature and severity of the disease/symptoms to be treated.

Formulations containing particles described herein can be prepared using a pharmaceutically acceptable carrier composed of materials that are considered safe and effective and can be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which can include plasticizers, pigments, colorants, stabilizing agents, and glidants. Delayed release, extended release, and/or pulsatile release dosage formulations can be prepared as described in standard references such as "Pharmaceutical dosage form tablets," eds. Liberman et. al. (New York, Marcel Dekker, Inc., 1989), "Remington—The science and practice of pharmacy," 20th ed., Lippincott Williams & Wilkins, Baltimore, Md., 2000, and "Pharmaceutical dosage forms and drug delivery systems," 6th Edition, Ansel et al., (Media, PA: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard decomposition reactions which include, by way of example, oxidative reactions.

A "pharmaceutical composition" or "pharmaceutically acceptable" composition, is defined as a therapeutically effective amount of one or more of the compositions described herein, formulated together with one or more pharmaceutically acceptable carriers (additives) and/or diluents. As described in detail, the pharmaceutical compositions of the present disclosure can be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The compositions of the present disclosure can be given in dosages, generally, at the maximum amount while avoiding or minimizing any potentially detrimental side effects. The compositions can be administered in effective amounts, alone or in a cocktail with other compounds, for example, other compounds that can be used to treat a disease. An effective amount is generally an amount sufficient to inhibit the disease within the subject.

One of skill in the art can determine what an effective amount of the composition is by screening the composition using known methods. The effective amounts may depend, of course, on factors such as the severity of the condition being treated; individual patient parameters including age, physical condition, size, and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

Actual dosage levels of the active ingredients in the pharmaceutical compositions of this disclosure can be varied so as to obtain an amount of the active ingredient that is effective to achieve the desired therapeutic response for a particular patient, composition, and mode of administration, without being toxic to the patient.

The selected dosage level may depend upon a variety of factors including the activity of the particular particles of the present disclosure employed, or the ester, salt or amide thereof, the route of administration, the time of administration, the rate of excretion or metabolism of the particular particles being employed, the duration of the treatment, other drugs, compounds and/or materials used in combination with the particular particles employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the particles of the disclosure employed in the pharmaceutical composition at levels lower than that required to achieve the desired therapeutic effect and then gradually increasing the dosage until the desired effect is achieved.

In some embodiments, particles or pharmaceutical composition of the disclosure is provided to a subject chronically. Chronic treatments include any form of repeated administration for an extended period of time, such as repeated administrations for one or more months, between a month and a year, one or more years, or longer. In many embodiments, a chronic treatment involves administering particles or pharmaceutical composition of the disclosure repeatedly over the life of the subject. For example, chronic treatments can involve regular administrations, for example one or more times a day, one or more times a week, or one or more times a month. In general, a suitable dose such as a daily dose of particles of the disclosure will be that amount of the particles that is the lowest dose effective to produce a therapeutic effect. Such an effective dose will generally depend upon the factors described above.

While it is possible for a composition of the present disclosure to be administered alone, it can be administered as a pharmaceutical formulation (composition) as described above.

EXAMPLES

Preparation and Purification of ATF-Toxin Fusion Protein:

A pseudomonas exotoxin A (PE38KDEL) has a potent anti-tumor effect. Upon entering into cells, highly toxic PE38 domain interacts with the translation elongation factor 2 to inhibit protein synthesis, leading to apoptotic cell death. This cell death is significantly different from all chemotherapy drugs that act through cellular DNA damage or blocking cell cycling. Although PE38 and other toxins have been evaluated as cancer therapeutic agents either by conjugating to antibodies or as fusion proteins, the major obstacle for clinical development is the presence severe systemic toxicity due to nonspecific distribution into normal tissues and organs. For recombination fusion protein mediated therapy, an additional issue is the short blood half-life that prevents efficient delivery into tumors. To address above issues, a tumor targeting ligand-toxin fusion proteins with was developed with dual receptor targeting and cell death-inducing function. The targeting-toxin ligand may conjugated to nanoparticles to be targeted delivered into tumor cells expressing those receptors, such as urokinase plasminogen activator receptor (uPAR) and epidermal growth factor receptor (EGFR). Nanoparticle-mediated delivery of PE38 toxin significantly reduced systemic toxicity while producing a strong antitumor growth effect.

Recombinant ATF-Toxin (PE38) was produced from a bacterial expression system using a ATF-Toxin fusion gene plasmid. For production of ATF-Toxin, a frozen vial of about 1 mL of bacterial stock containing ATF-Toxin plasmids was added into 50 mL of LB culture media (2.5% LB Broth media, 1% glucose and 100 ppb Ampicillin) and incubated overnight at 37° C. On the next day, the bacterial was transferred a 4 L flask with 1000 mL of LB culture media and cultured for about 3 h at 37° C. until the OD reading reaches 1.5~1.8. 100 μL of IPTG (1 μM) was then added and the bacterial was cultured for 2 h. The flask was put into ice bath for around half an hour and the bacterial was collected by centrifugation at 6000 rpm for 5 min. The collected bacterial was stored at −20° C.

For purification of ATF-Toxin, the bacterial was dissolved in 30 mL of lysis buffer (50 mM NaH2PO4, 1 M NaCl and 0.4 M Urea). Imidazole (10 mM) and appropriate amount of protease inhibitor were added into the buffer. The bacterial was sonicated for 30 min in ice bath and debris was removed by centrifugation at 18000 rpm for 30 min. The supernatant was collected and mixed with 1 mL of NTA-Ni-agarose beads (Qiagen, Miami, Fla.) for about 1 h at room temperature. The beads were collected by centrifugation at 2000 rpm for 5 min and were transferred into a purification column (Poly-Prep Chromatography Columns, BioRad, Hercules, Calif.). The column was firstly eluted with 30 mL of washing buffer (50 mM NaH2PO4, 1 M NaCl and 20 mM imidazole) to remove impurities and then with 2-5 mL of elution buffer (50 mM NaH2PO4, 0.3 M NaCl and 300 mM imidazole).

Production of uPAR Targeted ATF-Toxin or Dual uAPR and IGF1R Targeted IGF1-ATF-Toxin-IONP Carboxyl groups on the amphiphilic polymer-coated IONPs (core size: 10 nm) were activated by mixing with ethyl-3-dimethyl amino propyl carbodiimide (EDAC, Sigma-Aldrich) and N-hydroxysulfosuccinimide (sulfo-NHS, Sigma-Aldrich). NIR 830 dye-labeled fusion protein of ATF-PE38 (ATF-Toxin-Dye) alone or NIR 830 dye-labeled human recombinant IGF1 peptide (IGF1-Dye) in combination with NIR 830 dye—labeled fusion protein of ATF-PE38 (ATF-Toxin-Dye) were conjugated to the polymer coated IONPs mediated by an amid bond between carboxyl groups on the surface of the polymer and amine groups of IGF1 peptides or ATF-PE38 peptide (FIG. 3). Although interaction of ATF with uPAR on the cell surface can lead to endocytosis of ATF-Toxin, the level of uPAR expression is heterogeneous with a high level in the invasive tumor edge in both tumor cells and tumor stromal cells, and relatively low level in the tumor center. However, IGF-1R is highly expressed in all tumor cells. The combination of uPAR and IGF-1R targeting increases targeted delivery into tumor cells, especially in the tumor center.

In one example, 60 μg of EDAC and 40 μg of sulfo-NHS were added to the aqueous solution of 1 mg of IONPs in 10 mM borate buffer (pH 4.5), allowing activation of IONPs for 10 min. Activated IONPs were then collected by centrifugation at 3000 rpm for 10 min using Nanosep 100 K column (Pall Corporation, Port Washington, N.Y., USA) and then reacted with mixture of 75 μg of IGF1-Dye and 100 ug of ATF-Toxin-Dye in 10 mM borate buffer (pH 8.5) to produce ATF-Toxin-IONP or IGF1-ATF-Toxin-IONP. The reaction was carried out overnight (~12 h) at 4° C. or for 4 h at room temperature. The final ATF-Toxin-IONP or IGF1-ATF-Toxin-IONPs were purified using Nanosep 100 K column. Control non-targeting Toxin conjugated IONPs (NT-Toxin-IONPs) were prepared using a PE38 protein without targeting domain accordingly using same method.

In Vitro Cell Proliferation Assay

Human breast cancer cells derived from breast PDX tumors were cultured in 96-well plate at a density of 5,000 cells/well. After 24 h of plating, cells were washed once with cold PBS. Different Toxin-IONP conjugates were diluted in the culture medium at various toxin concentrations and then added into cell cultures. Unconjugated toxins were used as a treatment control. After incubating for 4 h when Toxin-IONP conjugates bound to and entered into tumor cells, cells were washed 3 times with cold PBS to remove unbound IONPs. 100 μL of fresh medium was then added to the plate. Cells were incubated for an additional 72 h and viability of the cells was determined by Alamar Blue assay (Life Technologies, NY). Cells treated with culture medium alone were used as the no treatment control. Results shown in FIG. 4 are the mean value of four repeat studies.

In Vivo Near-Infrared Fluorescence Optical Imaging

Mice were subjected to NIR optical imaging when tumor reached a size of about 6-8 mm in diameter. 400 picomolar (pmol) of IGF1-IONPs, ATF-Toxin-IONPs and IGF1-ATF-Toxin-IONPs were injected via the tail vein into the tumor bearing mice. NIR optical imaging was conducted using the Xenogen IVIS Spectrum imaging system (Caliper LIfe Sciences, Alameda, Calif.). Mice were sacrificed and tumors and normal organs were collected. All optical images were captured using 745 nm excitation and 820 nm emission filter set with 30 seconds exposure time. Optical Images were analyzed using the software provided by the Xenogen IVIS Spectrum imaging system. ROIs were selected for measuring the mean fluorescence intensity (MFI) of tumors and corresponding body background. Mice receiving IGF1-IONPs, ATF-Toxin-IONPs and IGF1-ATF-Toxin-IONPs all showed good IONP accumulation in the tumor sites.

In Vivo Antitumor Efficacy

Nude mice bearing orthotopic breast PDX tumors derived from the breast cancer Patient #9 tumor tissue (ER+, chemotherapy and Radiation resistant) were randomized into 4 experimental groups with 5 mice in each group, including no treatment control, NT-Toxin-IONPs, ATF-Toxin-IONP, and IGF1-ATF-Toxin-IONP. Treatment started when the tumor reached sizes of 6-8 mm at an ATF-toxin equivalent dose of 2 mg/kg body weight via the tail vein injection twice per week for 5 injections. Tumor volume and mouse body weight were monitored twice per week. Some of the tumors in the mice treated with targeted ATF-Toxin-IONP and IGF-ATF-Toxin-IONP turned to black color after 1st injection, suggesting induction of tumor necrosis. All tumors became black in those group after 4th treatment. However, this was not found in NT-Toxin-IONP treatment group. The tumors only became black when they reach certain size (over 1.5 cm diameter).

After each injection, a representative mouse from each group was selected for NIR optical imaging. The interesting thing for the mice receiving ATF-Toxin-IONP and IGF-ATF-Toxin-IONP is the tumors which had optical signals after 1st injection lose the optical signal after multiple treatment, while new grown tumor showed optical signal at the same time. This confirmed the induction of tumor necrosis for those groups.

Figure 5:
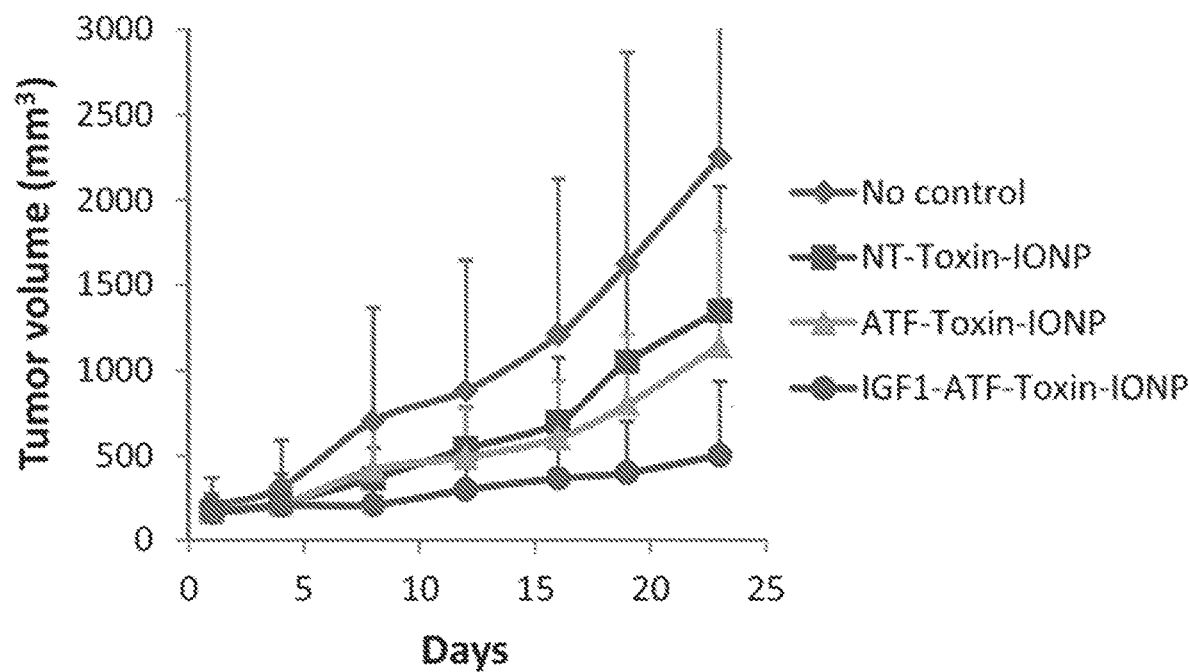
FIG. 5 shows data on in vivo antitumor effect in an orthotopic human breast PDX tumor model. Growth inhibition of breast PDX tumors by different treatments. Mice were i.v. administrated at a toxin dose of 2 mg/kg twice a week for 5 injections.

Tumors in all groups were collected by surgery 3 days after the final treatment and tumors were collected for histological, chemical, and immunofluorescence analyses. In comparison with the no treatment control group, the volumes of PDX tumors from the mice in all treated groups showed various degrees of tumor growth inhibition. We found that treatment with NT-Toxin-IONP and ATF-Toxin-IONP led to 40.2% and 49.2% of tumor growth inhibition, respectively, compared to the control group (FIG. 5). However, there was no statistically significant difference between those two groups with no treatment control (Student's t-test:

No treatment control vs NT-Toxin-IONP: p=0.113, No treatment control vs ATF-Toxin-IONP: p=0.088). In contrast, PDX tumors collected from the mice that treated with IGF1-ATF-Toxin-IONP were significantly smaller than those from the control groups of no treatment, or NT-Toxin-IONP treated group. There was 77.7% tumor volume growth inhibition in the IGF1-ATF-Toxin-IONP treated mouse group. Differences in tumor volumes among groups with different treatments were statistically significant (Student's t-test: No treatment control vs IGF1-ATF-Toxin-IONP p<0.03; NT-Toxin-IONP vs IGF1-ATF-Toxin-IONP p<0.02). Using loss of mouse body weight as an indication of system toxicity, there was no apparent systemic toxicity for all treatment groups following 5 treatments of 2 mg/kg of toxin equivalent doses.

Figure 6:
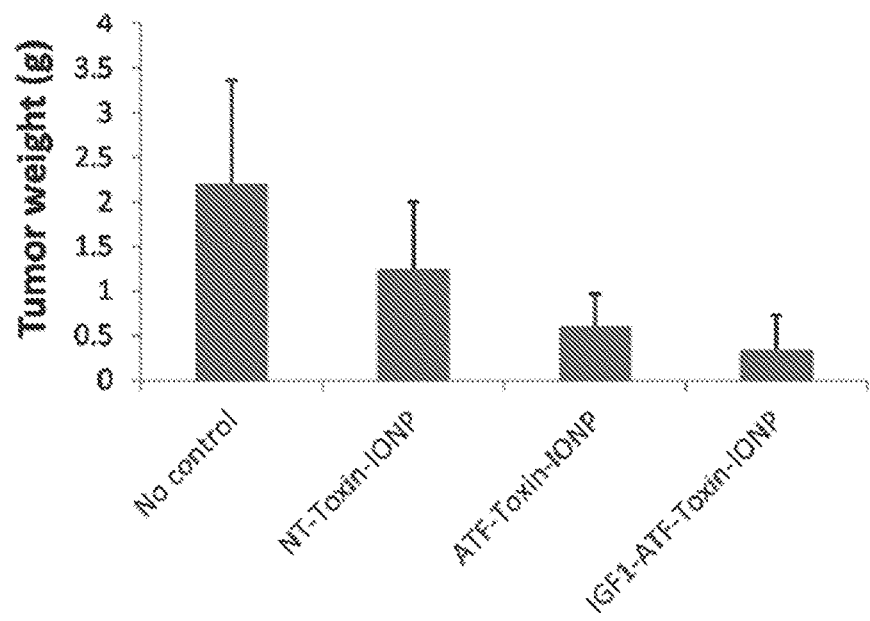
FIG. 6 shows data on mean tumor weight of each treatment group after surgical collection of the tumors.

In terms of tumor weights, similar results were found. Treatment with NT-Toxin-IONP, ATF-Toxin-IONP and IGF1-ATF-Toxin-IONP led to 43.3%, 72.1% and 84.3% of tumor growth inhibition, respectively, compared to the control group (FIG. 6). Statistically significant differences were found between both ATF-Toxin-IONP and IGF1-ATF-Toxin-IONP with no treatment control.

The invention claimed is:

1. A nanoparticle coated with a fusion peptide comprising NCDCLNGGTCVSNKYFSNIHWCNCPKKFGGQH-CEIDKSKGGGGSGAPEGGSLAALTAH QACHLPLETFTRHRQPRGWEQLEQCGYPVQRLVALY-LAARLSWNQVDQVIRNALASPG SGGDLGEAIREQPEQARLALTLAAAESER-FVRQGTGNDEAGAANGPADSGDALLERNY PTGAE-FLGDGGDVSFSTRGTQNWTVERLLQAHROLEER-GYFVGYHGTFLEAAQSIVFG GVRARSQDLDAIWRGFYIAGDPALAYGYAQDQEP-DARGRIRNGALLRVYVPRSSLPGF YRTSLT-LAAPEAAGEVERLIGHPLPLRLDAITGPEEEGGR-LETILGWPLAERTVVIPSAIPT DPRNVGGDLDPSSIPDKEQAIS-ALPDYASQPGKPPKDEL (SEQ ID NO: 1), and wherein the nanoparticle is further coated with a recombinant IGF1 peptide that binds insulin-like growth factor 1 receptor.

2. A pharmaceutical composition comprising a nanoparticle of claim 1 and a pharmaceutically acceptable excipient.

3. The nanoparticle of claim 1, further comprising a chemotherapy agent.

4. The nanoparticle of claim 3, wherein the chemotherapy agent is attached to a polymer around the core of the nanoparticle.

5. The nanoparticle of claim 3, wherein the chemotherapy agent is encapsulated by a polymer around the core of the particle.

6. The nanoparticle of claim 3, wherein the chemotherapy agent is doxorubicin.

7. The nanoparticle of claim 3, wherein the chemotherapy agent is cisplatin.

8. A nucleic acid sequence comprising a sequence encoding the fusion protein having SEQ ID NO: 1.

9. A vector comprising a nucleic acid sequence of claim 8.

10. A cell or cell free expression system comprising a vector of claim 9.

11. A method of treating cancer comprising administering an effective amount of a nanoparticle of claim 1 to a subject in need thereof.

12. The method of claim 11, wherein the cancer is carcinoma, lymphoma, blastoma, sarcoma, leukemia, non-small cell lung cancer, squamous cell cancer, small-cell lung cancer, peritoneum cancer, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial cancer, uterine, salivary gland cancer, kidney cancer, liver cancer, prostate cancer, vulval cancer, thyroid cancer, hepatic cancer, head cancer, neck cancer, or leukemia.

\* \* \* \* \*

SEQUENCE LISTING

<160> NUMBER OF SEQ ID NOS: 12

<210> SEQ ID NO 1
<211> LENGTH: 391
<212> TYPE: PRT
<213> ORGANISM: Artificial
<220> FEATURE:
<223> OTHER INFORMATION: Synthetic construct

<400> SEQUENCE: 1

```
Asn Cys Asp Cys Leu Asn Gly Gly Thr Cys Val Ser Asn Lys Tyr Phe
1               5                   10                  15

Ser Asn Ile His Trp Cys Asn Cys Pro Lys Lys Phe Gly Gly Gln His
            20                  25                  30

Cys Glu Ile Asp Lys Ser Lys Gly Gly Gly Ser Gly Ala Pro Glu
        35                  40                  45

Gly Gly Ser Leu Ala Ala Leu Thr Ala His Gln Ala Cys His Leu Pro
    50                  55                  60

Leu Glu Thr Phe Thr Arg His Arg Gln Pro Arg Gly Trp Glu Gln Leu
65                  70                  75                  80

Glu Gln Cys Gly Tyr Pro Val Gln Arg Leu Val Ala Leu Tyr Leu Ala
                85                  90                  95

Ala Arg Leu Ser Trp Asn Gln Val Asp Gln Val Ile Arg Asn Ala Leu
            100                 105                 110

Ala Ser Pro Gly Ser Gly Gly Asp Leu Gly Glu Ala Ile Arg Glu Gln
        115                 120                 125

Pro Glu Gln Ala Arg Leu Ala Leu Thr Leu Ala Ala Ala Glu Ser Glu
    130                 135                 140

Arg Phe Val Arg Gln Gly Thr Gly Asn Asp Glu Ala Gly Ala Ala Asn
145                 150                 155                 160

Gly Pro Ala Asp Ser Gly Asp Ala Leu Leu Glu Arg Asn Tyr Pro Thr
                165                 170                 175

Gly Ala Glu Phe Leu Gly Asp Gly Gly Asp Val Ser Phe Ser Thr Arg
            180                 185                 190

Gly Thr Gln Asn Trp Thr Val Glu Arg Leu Leu Gln Ala His Arg Gln
        195                 200                 205
```

```
Leu Glu Glu Arg Gly Tyr Phe Val Gly Tyr His Gly Thr Phe Leu Glu
210                 215                 220
Ala Ala Gln Ser Ile Val Phe Gly Gly Val Arg Ala Arg Ser Gln Asp
225                 230                 235                 240
Leu Asp Ala Ile Trp Arg Gly Phe Tyr Ile Ala Gly Asp Pro Ala Leu
            245                 250                 255
Ala Tyr Gly Tyr Ala Gln Asp Gln Glu Pro Asp Ala Arg Gly Arg Ile
            260                 265                 270
Arg Asn Gly Ala Leu Leu Arg Val Tyr Val Pro Arg Ser Ser Leu Pro
        275                 280                 285
Gly Phe Tyr Arg Thr Ser Leu Thr Leu Ala Ala Pro Glu Ala Ala Gly
    290                 295                 300
Glu Val Glu Arg Leu Ile Gly His Pro Leu Pro Leu Arg Leu Asp Ala
305                 310                 315                 320
Ile Thr Gly Pro Glu Glu Gly Gly Arg Leu Glu Thr Ile Leu Gly
            325                 330                 335
Trp Pro Leu Ala Glu Arg Thr Val Val Ile Pro Ser Ala Ile Pro Thr
            340                 345                 350
Asp Pro Arg Asn Val Gly Gly Asp Leu Asp Pro Ser Ser Ile Pro Asp
        355                 360                 365
Lys Glu Gln Ala Ile Ser Ala Leu Pro Asp Tyr Ala Ser Gln Pro Gly
370                 375                 380
Lys Pro Pro Lys Asp Glu Leu
385                 390

<210> SEQ ID NO 2
<211> LENGTH: 1284
<212> TYPE: DNA
<213> ORGANISM: Artificial
<220> FEATURE:
<223> OTHER INFORMATION: Synthetic construct

<400> SEQUENCE: 2
atgggcagca gccatcatca tcatcatcac aactgtgact gtctaaatgg aggaacatgt      60
gtgtccaaca gtacttctc caacattcac tggtgcaact gcccaaagaa attcggaggg     120
cagcactgtg aaatagataa gtcaaaagga ggtggaggat caggcgcgcc cgagggcggc     180
agcctggccg cgctgaccgc gcaccaggct tgccacctgc cgctggagac tttcaccgt     240
catcgccagc cgcgcggctg ggaacaactg gagcagtgcg gctatccggt gcagcggctg     300
gtcgccctct acctggcggc gcggctgtcg tggaaccagg tcgaccaggt gatccgcaac     360
gccctggcca gccccggcag cggcggcgac ctgggcgaag cgatccgcga gcagccggag     420
caagcccgtc tggccctgac cctggccgcc gccgagagcg agcgcttcgt ccggcagggc     480
actggcaacg acgaggccgg cgcggccaac ggcccggcgg acagcggcga cgccctgctg     540
gagcgcaact atcccactgg cgcggagttc ctcggcgacg cgggcgacgt cagcttcagc     600
acccgcggca cgcagaactg gacggtggag cggctgctcc aggcgcaccg ccaactggag     660
gagcgcggct atgtgttcgt cggctaccac ggcaccttcc tcgaagcggc gcaaagcatc     720
gtcttcggcg gggtgcgcgc gcgcagccag gacctcgacg cgatctggcg cggtttctat     780
atcgccggcg atccggcgct ggcctacggc tacgcccagg accaggaacc cgacgcacgc     840
ggccggatcc gcaacggtgc cctgctgcgg gtctatgtgc cgcgctcgag cctgccgggc     900
ttctaccgca ccagcctgac cctggccgcg ccggaggcgg cgggcgaggt cgaacggctg     960
atcggccatc cgctgccgct gcgcctggac gccatcaccg gccccgagga ggaaggcggg    1020
```

```
cgcctggaga ccattctcgg ctggccgctg gccgagcgca ccgtggtgat tccctcggcg    1080
atccccaccg acccgcgcaa cgtcggcggc gacctcgacc cgtccagcat ccccgacaag    1140
gaacaggcga tcagcgccct gccggactac gccagccagc ccggcaaacc gccgaaagac    1200
gaactgtaaa agggcgagct caattcgaag cttgcggccg cactcgagca ccaccaccac    1260
caccactgag atccggctgc taac                                          1284
```

<210> SEQ ID NO 3
<211> LENGTH: 425
<212> TYPE: PRT
<213> ORGANISM: Artificial
<220> FEATURE:
<223> OTHER INFORMATION: Synthetic construct

<400> SEQUENCE: 3

```
Met Gly Ser Ser His His His His His Asn Cys Asp Cys Leu Asn
1               5                   10                  15

Gly Gly Thr Cys Val Ser Asn Lys Tyr Phe Ser Asn Ile His Trp Cys
            20                  25                  30

Asn Cys Pro Lys Lys Phe Gly Gly Gln His Cys Glu Ile Asp Lys Ser
        35                  40                  45

Lys Gly Gly Gly Ser Gly Ala Pro Glu Gly Gly Ser Leu Ala Ala
    50                  55                  60

Leu Thr Ala His Gln Ala Cys His Leu Pro Leu Glu Thr Phe Thr Arg
65                  70                  75                  80

His Arg Gln Pro Arg Gly Trp Glu Gln Leu Glu Gln Cys Gly Tyr Pro
                85                  90                  95

Val Gln Arg Leu Val Ala Leu Tyr Leu Ala Ala Arg Leu Ser Trp Asn
            100                 105                 110

Gln Val Asp Gln Val Ile Arg Asn Ala Leu Ala Ser Pro Gly Ser Gly
        115                 120                 125

Gly Asp Leu Gly Glu Ala Ile Arg Glu Gln Pro Glu Gln Ala Arg Leu
    130                 135                 140

Ala Leu Thr Leu Ala Ala Ala Glu Ser Glu Arg Phe Val Arg Gln Gly
145                 150                 155                 160

Thr Gly Asn Asp Glu Ala Gly Ala Ala Asn Gly Pro Ala Asp Ser Gly
                165                 170                 175

Asp Ala Leu Leu Glu Arg Asn Tyr Pro Thr Gly Ala Glu Phe Leu Gly
            180                 185                 190

Asp Gly Gly Asp Val Ser Phe Ser Thr Arg Gly Thr Gln Asn Trp Thr
        195                 200                 205

Val Glu Arg Leu Leu Gln Ala His Arg Gln Leu Glu Glu Arg Gly Tyr
    210                 215                 220

Phe Val Gly Tyr His Gly Thr Phe Leu Glu Ala Ala Gln Ser Ile Val
225                 230                 235                 240

Phe Gly Gly Val Arg Ala Arg Ser Gln Asp Leu Asp Ala Ile Trp Arg
                245                 250                 255

Gly Phe Tyr Ile Ala Gly Asp Pro Ala Leu Ala Tyr Gly Tyr Ala Gln
            260                 265                 270

Asp Gln Glu Pro Asp Ala Arg Gly Arg Ile Arg Asn Gly Ala Leu Leu
        275                 280                 285

Arg Val Tyr Val Pro Arg Ser Ser Leu Pro Gly Phe Tyr Arg Thr Ser
    290                 295                 300
```

```
Leu Thr Leu Ala Ala Pro Glu Ala Gly Glu Val Glu Arg Leu Ile
305                 310                 315                 320

Gly His Pro Leu Pro Leu Arg Leu Asp Ala Ile Thr Gly Pro Glu Glu
                325                 330                 335

Glu Gly Gly Arg Leu Glu Thr Ile Leu Gly Trp Pro Leu Ala Glu Arg
            340                 345                 350

Thr Val Val Ile Pro Ser Ala Ile Pro Thr Asp Pro Arg Asn Val Gly
                355                 360                 365

Gly Asp Leu Asp Pro Ser Ser Ile Pro Asp Lys Glu Gln Ala Ile Ser
370                 375                 380

Ala Leu Pro Asp Tyr Ala Ser Gln Pro Gly Lys Pro Pro Lys Asp Glu
385                 390                 395                 400

Leu Lys Gly Glu Leu Asn Ser Lys Leu Ala Ala Leu Glu His His
                405                 410                 415

His His His His Asp Pro Ala Ala Asn
                420                 425

<210> SEQ ID NO 4
<211> LENGTH: 475
<212> TYPE: PRT
<213> ORGANISM: Artificial
<220> FEATURE:
<223> OTHER INFORMATION: Synthetic construct

<400> SEQUENCE: 4

Met Gly Ser Ser His His His His His His Thr Ser Glu Ile Val Met
1               5                   10                  15

Thr Gln Ser Pro Ala Thr Leu Ser Leu Ser Pro Gly Glu Arg Ala Thr
                20                  25                  30

Leu Ser Cys Arg Ala Ser Gln Ser Val Ser Ser Tyr Leu Ala Trp Tyr
            35                  40                  45

Gln Gln Lys Pro Gly Gln Ala Pro Arg Leu Leu Ile Tyr Asp Ala Ser
        50                  55                  60

Asn Arg Ala Thr Gly Ile Pro Ala Arg Phe Ser Gly Ser Gly Ser Gly
65                  70                  75                  80

Thr Asp Phe Thr Leu Thr Ile Ser Arg Leu Glu Pro Glu Asp Phe Ala
                85                  90                  95

Val Tyr Tyr Cys Gln Gln Tyr Gly Ser Ser Pro Ile Thr Phe Gly Gln
            100                 105                 110

Gly Thr Arg Leu Glu Ile Lys Arg Ser Ser Gly Gly Gly Gly Ser Gly
        115                 120                 125

Ala Pro Glu Gly Gly Ser Leu Ala Ala Leu Thr Ala His Gln Ala Cys
130                 135                 140

His Leu Pro Leu Glu Thr Phe Thr Arg His Arg Gln Pro Arg Gly Trp
145                 150                 155                 160

Glu Gln Leu Glu Gln Cys Gly Tyr Pro Val Gln Arg Leu Val Ala Leu
                165                 170                 175

Tyr Leu Ala Ala Arg Leu Ser Trp Asn Gln Val Asp Gln Val Ile Arg
            180                 185                 190

Asn Ala Leu Ala Ser Pro Gly Ser Gly Gly Asp Leu Gly Glu Ala Ile
        195                 200                 205

Arg Glu Gln Pro Glu Gln Ala Arg Leu Ala Leu Thr Leu Ala Ala Ala
    210                 215                 220

Glu Ser Glu Arg Phe Val Arg Gln Gly Thr Gly Asn Asp Glu Ala Gly
225                 230                 235                 240
```

-continued

```
Ala Ala Asn Gly Pro Ala Asp Ser Gly Asp Ala Leu Leu Glu Arg Asn
            245                 250                 255

Tyr Pro Thr Gly Ala Glu Phe Leu Gly Asp Gly Asp Val Ser Phe
        260                 265                 270

Ser Thr Arg Gly Thr Gln Asn Trp Thr Val Glu Arg Leu Leu Gln Ala
        275                 280                 285

His Arg Gln Leu Glu Glu Arg Gly Tyr Val Phe Val Gly Tyr His Gly
    290                 295                 300

Thr Phe Leu Glu Ala Ala Gln Ser Ile Val Phe Gly Val Arg Ala
305                 310                 315                 320

Arg Ser Gln Asp Leu Asp Ala Ile Trp Arg Gly Phe Tyr Ile Ala Gly
                325                 330                 335

Asp Pro Ala Leu Ala Tyr Gly Tyr Ala Gln Asp Gln Glu Pro Asp Ala
                340                 345                 350

Arg Gly Arg Ile Arg Asn Gly Ala Leu Leu Arg Val Tyr Val Pro Arg
            355                 360                 365

Ser Ser Leu Pro Gly Phe Tyr Arg Thr Ser Leu Thr Leu Ala Ala Pro
    370                 375                 380

Glu Ala Ala Gly Glu Val Glu Arg Leu Ile Gly His Pro Leu Pro Leu
385                 390                 395                 400

Arg Leu Asp Ala Ile Thr Gly Pro Glu Glu Gly Arg Leu Glu
                405                 410                 415

Thr Ile Leu Gly Trp Pro Leu Ala Glu Arg Thr Val Val Ile Pro Ser
                420                 425                 430

Ala Ile Pro Thr Asp Pro Arg Asn Val Gly Gly Asp Leu Asp Pro Ser
                435                 440                 445

Ser Ile Pro Asp Lys Glu Gln Ala Ile Ser Ala Leu Pro Asp Tyr Ala
    450                 455                 460

Ser Gln Pro Gly Lys Pro Lys Asp Glu Leu
465                 470                 475

<210> SEQ ID NO 5
<211> LENGTH: 459
<212> TYPE: PRT
<213> ORGANISM: Artificial
<220> FEATURE:
<223> OTHER INFORMATION: Synthetic construct

<400> SEQUENCE: 5

Thr Gln Ser Pro Ala Thr Leu Ser Leu Ser Pro Gly Glu Arg Ala Thr
1               5                   10                  15

Leu Ser Cys Arg Ala Ser Gln Ser Val Ser Ser Tyr Leu Ala Trp Tyr
            20                  25                  30

Gln Gln Lys Pro Gly Gln Ala Pro Arg Leu Leu Ile Tyr Asp Ala Ser
        35                  40                  45

Asn Arg Ala Thr Gly Ile Pro Ala Arg Phe Ser Gly Ser Gly Ser Gly
    50                  55                  60

Thr Asp Phe Thr Leu Thr Ile Ser Arg Leu Glu Pro Glu Asp Phe Ala
65                  70                  75                  80

Val Tyr Tyr Cys Gln Gln Tyr Gly Ser Ser Pro Ile Thr Phe Gly Gln
                85                  90                  95

Gly Thr Arg Leu Glu Ile Lys Arg Ser Ser Gly Gly Gly Ser Gly
            100                 105                 110

Ala Pro Glu Gly Gly Ser Leu Ala Ala Leu Thr Ala His Gln Ala Cys
        115                 120                 125
```

His Leu Pro Leu Glu Thr Phe Thr Arg His Arg Gln Pro Arg Gly Trp
            130                 135                 140

Glu Gln Leu Glu Gln Cys Gly Tyr Pro Val Gln Arg Leu Val Ala Leu
145                 150                 155                 160

Tyr Leu Ala Ala Arg Leu Ser Trp Asn Gln Val Asp Gln Val Ile Arg
                165                 170                 175

Asn Ala Leu Ala Ser Pro Gly Ser Gly Gly Asp Leu Gly Glu Ala Ile
                180                 185                 190

Arg Glu Gln Pro Glu Gln Ala Arg Leu Ala Leu Thr Leu Ala Ala Ala
            195                 200                 205

Glu Ser Glu Arg Phe Val Arg Gln Gly Thr Gly Asn Asp Glu Ala Gly
            210                 215                 220

Ala Ala Asn Gly Pro Ala Asp Ser Gly Asp Ala Leu Leu Glu Arg Asn
225                 230                 235                 240

Tyr Pro Thr Gly Ala Glu Phe Leu Gly Asp Gly Asp Val Ser Phe
                245                 250                 255

Ser Thr Arg Gly Thr Gln Asn Trp Thr Val Glu Arg Leu Leu Gln Ala
                260                 265                 270

His Arg Gln Leu Glu Glu Arg Gly Tyr Val Phe Val Gly Tyr His Gly
            275                 280                 285

Thr Phe Leu Glu Ala Ala Gln Ser Ile Val Phe Gly Gly Val Arg Ala
            290                 295                 300

Arg Ser Gln Asp Leu Asp Ala Ile Trp Arg Gly Phe Tyr Ile Ala Gly
305                 310                 315                 320

Asp Pro Ala Leu Ala Tyr Gly Tyr Ala Gln Asp Gln Glu Pro Asp Ala
                325                 330                 335

Arg Gly Arg Ile Arg Asn Gly Ala Leu Leu Arg Val Tyr Val Pro Arg
                340                 345                 350

Ser Ser Leu Pro Gly Phe Tyr Arg Thr Ser Leu Thr Leu Ala Ala Pro
            355                 360                 365

Glu Ala Ala Gly Glu Val Glu Arg Leu Ile Gly His Pro Leu Pro Leu
            370                 375                 380

Arg Leu Asp Ala Ile Thr Gly Pro Glu Glu Gly Gly Arg Leu Glu
385                 390                 395                 400

Thr Ile Leu Gly Trp Pro Leu Ala Glu Arg Thr Val Val Ile Pro Ser
                405                 410                 415

Ala Ile Pro Thr Asp Pro Arg Asn Val Gly Gly Asp Leu Asp Pro Ser
                420                 425                 430

Ser Ile Pro Asp Lys Glu Gln Ala Ile Ser Ala Leu Pro Asp Tyr Ala
            435                 440                 445

Ser Gln Pro Gly Lys Pro Pro Lys Asp Glu Leu
    450                 455

<210> SEQ ID NO 6
<211> LENGTH: 135
<212> TYPE: PRT
<213> ORGANISM: Artificial
<220> FEATURE:
<223> OTHER INFORMATION: Synthetic construct

<400> SEQUENCE: 6

Ser Asn Glu Leu His Gln Val Pro Ser Asn Cys Asp Cys Leu Asn Gly
1               5                   10                  15

Gly Thr Cys Val Ser Asn Lys Tyr Phe Ser Asn Ile His Trp Cys Asn
                20                  25                  30

```
Cys Pro Lys Lys Phe Gly Gly Gln His Cys Glu Ile Asp Lys Ser Lys
        35                  40                  45

Thr Cys Tyr Glu Gly Asn Gly His Phe Tyr Arg Gly Lys Ala Ser Thr
    50                  55                  60

Asp Thr Met Gly Arg Pro Cys Leu Pro Trp Asn Ser Ala Thr Val Leu
65                  70                  75                  80

Gln Gln Thr Tyr His Ala His Arg Ser Asp Ala Leu Gln Leu Gly Leu
                85                  90                  95

Gly Lys His Asn Tyr Cys Arg Asn Pro Asp Asn Arg Arg Arg Pro Trp
            100                 105                 110

Cys Tyr Val Gln Val Gly Leu Lys Pro Leu Val Gln Glu Cys Met Val
            115                 120                 125

His Asp Cys Ala Asp Gly Lys
            130             135
```

<210> SEQ ID NO 7
<211> LENGTH: 68
<212> TYPE: PRT
<213> ORGANISM: Artificial
<220> FEATURE:
<223> OTHER INFORMATION: Synthetic construct

<400> SEQUENCE: 7

```
Ser Asn Glu Leu His Gln Val Pro Ser Asn Cys Asp Cys Leu Asn Gly
1               5                   10                  15

Gly Thr Cys Val Ser Asn Lys Tyr Phe Ser Asn Ile His Trp Cys Asn
            20                  25                  30

Cys Pro Lys Lys Phe Gly Gly Gln His Cys Glu Ile Asp Lys Ser Lys
        35                  40                  45

Thr Cys Tyr Glu Gly Asn Gly His Phe Tyr Arg Gly Lys Ala Ser Thr
    50                  55                  60

Asp Thr Met Gly
65
```

<210> SEQ ID NO 8
<211> LENGTH: 39
<212> TYPE: PRT
<213> ORGANISM: Artificial
<220> FEATURE:
<223> OTHER INFORMATION: Synthetic construct

<400> SEQUENCE: 8

```
Asn Cys Asp Cys Leu Asn Gly Gly Thr Cys Val Ser Asn Lys Tyr Phe
1               5                   10                  15

Ser Asn Ile His Trp Cys Asn Cys Pro Lys Lys Phe Gly Gly Gln His
            20                  25                  30

Cys Glu Ile Asp Lys Ser Lys
        35
```

<210> SEQ ID NO 9
<211> LENGTH: 111
<212> TYPE: PRT
<213> ORGANISM: Artificial
<220> FEATURE:
<223> OTHER INFORMATION: Synthetic construct

<400> SEQUENCE: 9

```
Thr Ser Glu Ile Val Met Thr Gln Ser Pro Ala Thr Leu Ser Leu Ser
1               5                   10                  15
```

```
Pro Gly Glu Arg Ala Thr Leu Ser Cys Arg Ala Ser Gln Ser Val Ser
                20                  25                  30

Ser Tyr Leu Ala Trp Tyr Gln Gln Lys Pro Gly Gln Ala Pro Arg Leu
            35                  40                  45

Leu Ile Tyr Asp Ala Ser Asn Arg Ala Thr Gly Ile Pro Ala Arg Phe
        50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Gln Gln Tyr Gly Ser Ser
                85                  90                  95

Pro Ile Thr Phe Gly Gln Gly Thr Arg Leu Glu Ile Lys Arg Ser
            100                 105                 110
```

<210> SEQ ID NO 10
<211> LENGTH: 153
<212> TYPE: PRT
<213> ORGANISM: Artificial
<220> FEATURE:
<223> OTHER INFORMATION: Synthetic construct

<400> SEQUENCE: 10

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
                20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
        50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
130                 135                 140

Ser Ala Gly Asn Lys Asn Tyr Arg Met
145                 150
```

<210> SEQ ID NO 11
<211> LENGTH: 338
<212> TYPE: PRT
<213> ORGANISM: Artificial
<220> FEATURE:
<223> OTHER INFORMATION: Synthetic construct

<400> SEQUENCE: 11

```
Glu Gly Gly Ser Leu Ala Ala Leu Thr Ala His Gln Ala Cys His Leu
1               5                   10                  15

Pro Leu Glu Thr Phe Thr Arg His Arg Gln Pro Arg Gly Trp Glu Gln
                20                  25                  30

Leu Glu Gln Cys Gly Tyr Pro Val Gln Arg Leu Val Ala Leu Tyr Leu
            35                  40                  45

Ala Ala Arg Leu Ser Trp Asn Gln Val Asp Gln Val Ile Arg Asn Ala
        50                  55                  60
```

```
Leu Ala Ser Pro Gly Ser Gly Gly Asp Leu Gly Glu Ala Ile Arg Glu
 65                  70                  75                  80

Gln Pro Glu Gln Ala Arg Leu Ala Leu Thr Leu Ala Ala Ala Glu Ser
             85                  90                  95

Glu Arg Phe Val Arg Gln Gly Thr Gly Asn Asp Glu Ala Gly Ala Ala
            100                 105                 110

Asn Gly Pro Ala Asp Ser Gly Asp Ala Leu Leu Glu Arg Asn Tyr Pro
        115                 120                 125

Thr Gly Ala Glu Phe Leu Gly Asp Gly Gly Asp Val Ser Phe Ser Thr
    130                 135                 140

Arg Gly Thr Gln Asn Trp Thr Val Glu Arg Leu Leu Gln Ala His Arg
145                 150                 155                 160

Gln Leu Glu Glu Arg Gly Tyr Val Phe Val Gly Tyr His Gly Thr Phe
                165                 170                 175

Leu Glu Ala Ala Gln Ser Ile Val Phe Gly Gly Val Arg Ala Arg Ser
            180                 185                 190

Gln Asp Leu Asp Ala Ile Trp Arg Gly Phe Tyr Ile Ala Gly Asp Pro
        195                 200                 205

Ala Leu Ala Tyr Gly Tyr Ala Gln Asp Gln Glu Pro Asp Ala Arg Gly
    210                 215                 220

Arg Ile Arg Asn Gly Ala Leu Leu Arg Val Tyr Val Pro Arg Ser Ser
225                 230                 235                 240

Leu Pro Gly Phe Tyr Arg Thr Ser Leu Thr Leu Ala Ala Pro Glu Ala
                245                 250                 255

Ala Gly Glu Val Glu Arg Leu Ile Gly His Pro Leu Pro Leu Arg Leu
            260                 265                 270

Asp Ala Ile Thr Gly Pro Glu Glu Gly Gly Arg Leu Glu Thr Ile
        275                 280                 285

Leu Gly Trp Pro Leu Ala Glu Arg Thr Val Val Ile Pro Ser Ala Ile
    290                 295                 300

Pro Thr Asp Pro Arg Asn Val Gly Gly Asp Leu Asp Pro Ser Ser Ile
305                 310                 315                 320

Pro Asp Lys Glu Gln Ala Ile Ser Ala Leu Pro Asp Tyr Ala Ser Gln
                325                 330                 335

Pro Gly

<210> SEQ ID NO 12
<211> LENGTH: 4
<212> TYPE: PRT
<213> ORGANISM: Artificial
<220> FEATURE:
<223> OTHER INFORMATION: Synthetic construct

<400> SEQUENCE: 12

Gly Phe Leu Gly
1
```